United States Patent
Kim

(10) Patent No.: US 7,668,665 B2
(45) Date of Patent: *Feb. 23, 2010

(54) METHODS OF NETWORKING INTERROGATION DEVICES FOR STRUCTURAL CONDITIONS

(75) Inventor: Hyeung-Yun Kim, Palo Alto, CA (US)

(73) Assignee: Advanced Structure Monitoring, Inc., Cupertino, CA (US)

( * ) Notice: Subject to any disclaimer, the term of this patent is extended or adjusted under 35 U.S.C. 154(b) by 17 days.

This patent is subject to a terminal disclaimer.

(21) Appl. No.: 11/509,198

(22) Filed: Aug. 23, 2006

(65) Prior Publication Data

US 2006/0287842 A1    Dec. 21, 2006

Related U.S. Application Data

(63) Continuation-in-part of application No. 10/942,714, filed on Sep. 16, 2004, now Pat. No. 7,286,964.

(60) Provisional application No. 60/505,120, filed on Sep. 22, 2003.

(51) Int. Cl.
*G01H 17/00* (2006.01)
*G06F 17/00* (2006.01)

(52) U.S. Cl. .............................. 702/33; 702/34; 702/35; 702/39; 73/584; 73/618

(58) Field of Classification Search .................. 702/33, 702/34, 35, 39
See application file for complete search history.

(56) References Cited

U.S. PATENT DOCUMENTS

| | | | |
|---|---|---|---|
| 2,177,629 | A | 10/1939 | Foster |
| 3,427,481 | A | 2/1969 | Lenahan et al. |
| 3,593,048 | A | 7/1971 | Dunegan et al. |

(Continued)

FOREIGN PATENT DOCUMENTS

KR    1020040007855    8/2005

(Continued)

OTHER PUBLICATIONS

Kim, H.Y. and Hwang, W. "*Estimation Of Normal Mode And Other System Parameters Of Composite Laminated Plates*", Composite Structures, 2001.

(Continued)

*Primary Examiner*—Hal D Wachsman
(74) *Attorney, Agent, or Firm*—Patent Office of Dr. Chung S. Park

(57) ABSTRACT

Methods of operating an interrogation system that has a plurality of patches attached to a host structure. Each patch is capable of generating a diagnostic wave and/or developing a sensor signal in response to the diagnostic wave. In each method, a Euclidean undirected graph is generated by forming a plurality of paths; wherein each path connects two of the patches and the length of the path is shorter than a preset limit. Then, a directed graph or network is generated by assigning a propagation direction of the diagnostic wave to each path. Structural condition index (SCI) values are measured by use of the directed graph and, based on the SCI values, the host structure is scanned for anomalies. The directed graph is reconfigured to determine the shape and location of the anomalies.

45 Claims, 17 Drawing Sheets

U.S. PATENT DOCUMENTS

| | | | |
|---|---|---|---|
| 4,011,472 A | 3/1977 | Feng | |
| 4,012,952 A | 3/1977 | Dory | |
| 4,297,887 A | 11/1981 | Bucaro | |
| 4,480,480 A | 11/1984 | Scott et al. | |
| 4,534,222 A | 8/1985 | Finch et al. | |
| 4,665,750 A | 5/1987 | Rogers | |
| 4,773,758 A | 9/1988 | Shaw | |
| 4,961,176 A | 10/1990 | Tanaka et al. | |
| 5,184,516 A | 2/1993 | Blazic et al. | |
| 5,195,046 A | 3/1993 | Gerardi et al. | |
| 5,440,300 A | 8/1995 | Spillman, Jr. | |
| 5,452,264 A | 9/1995 | Holroyd | |
| 5,519,381 A * | 5/1996 | Marsh et al. | 340/10.2 |
| 5,524,491 A | 6/1996 | Cavalloni | |
| 5,524,625 A | 6/1996 | Okazaki et al. | |
| 5,625,150 A | 4/1997 | Greene et al. | |
| 5,663,504 A | 9/1997 | Kluft | |
| 5,677,488 A | 10/1997 | Monahan et al. | |
| 5,710,723 A | 1/1998 | Hoth et al. | |
| 5,814,729 A | 9/1998 | Wu et al. | |
| 5,838,439 A | 11/1998 | Zang et al. | |
| 5,854,994 A | 12/1998 | Canada et al. | |
| 5,870,564 A * | 2/1999 | Jensen et al. | 709/241 |
| 6,047,331 A * | 4/2000 | Medard et al. | 709/239 |
| 6,115,653 A | 9/2000 | Bergstrom et al. | |
| 6,137,621 A | 10/2000 | Wu | |
| 6,144,790 A | 11/2000 | Biedin | |
| 6,161,434 A | 12/2000 | Fink et al. | |
| 6,170,334 B1 | 1/2001 | Paulson | |
| 6,182,512 B1 | 2/2001 | Lorraine | |
| 6,204,920 B1 | 3/2001 | Ellerbrock et al. | |
| 6,305,227 B1 | 10/2001 | Wu et al. | |
| 6,346,985 B1 | 2/2002 | Hall | |
| 6,347,256 B1 * | 2/2002 | Smirnov et al. | 700/100 |
| 6,370,964 B1 * | 4/2002 | Chang et al. | 73/862.046 |
| 6,377,014 B1 | 4/2002 | Gomi et al. | |
| 6,396,262 B2 | 5/2002 | Light et al. | |
| 6,399,939 B1 | 6/2002 | Sundaresan et al. | |
| 7,117,742 B2 | 10/2006 | Kim | |
| 7,197,931 B2 | 4/2007 | Kim | |
| 7,246,521 B2 | 7/2007 | Kim | |
| 7,281,428 B2 | 10/2007 | Kim | |
| 7,286,964 B2 * | 10/2007 | Kim | 702/183 |
| 7,322,244 B2 | 1/2008 | Kim | |
| 7,325,456 B2 | 2/2008 | Kim | |
| 2002/0012478 A1 | 1/2002 | Thirion et al. | |
| 2004/0206187 A1 | 10/2004 | Williams | |
| 2005/0002276 A1 | 1/2005 | Yogeswaren | |
| 2006/0152735 A1 | 7/2006 | Kageyama et al. | |
| 2006/0179949 A1 | 8/2006 | Kim | |

FOREIGN PATENT DOCUMENTS

KR  1020040022036  10/2005

OTHER PUBLICATIONS

Kim, H.Y., "*Structural Dynamic System Reconstruction Method For Vibrating Structures*", Transaction of ASME, 2003.

Kim, H.Y., "*Vibration-Based Damage Identification Using Reconstructed FRFS In Composite Structures*", Journal of Sound and Vibration, 2003.

Kim, H.Y. and Hwang, W., "*Effect of Debonding On Natural Frequencies And Frequency Response Functions Of Honeycomb Sandwich Beams*", Composite Structures, 2001.

Moon, T.C., Kim, H.Y. and Hwang W., "*Natural-Frequency Reduction Model For Matrix-Dominated Fatigue Damage in Composite Laminates*", Composite Structures, 2003.

* cited by examiner

METHODS OF NETWORKING INTERROGATION DEVICES FOR STRUCTURAL CONDITIONS

CROSS REFERENCE TO RELATED APPLICATIONS

This application is a continuation-in-part of application Ser. No. 10/942,714, filed on Sep. 16, 2004 and issued as U.S. Pat. No. 7,286,964, which claims the benefit of U.S. Provisional Application No. 60/505,120, filed on Sep. 22, 2003.

BACKGROUND

The present invention relates to diagnostics of structures, and more particularly to diagnostic network patch (DNP) systems for monitoring structural conditions.

In general, structures in service may require periodic inspections and appropriate maintenance services to prolong their life and/or to prevent catastrophic failures. Numerous methods have been employed to identify fault or damage of structures, where these methods may include conventional visual inspection and non-destructive techniques, such as ultrasonic and eddy current scanning, acoustic emission and X-ray inspection. These conventional methods require at least temporary removal of structures from service for inspection. Although still used for inspection of isolated locations, they are time-consuming and expensive.

With the advance of sensor technologies, several diagnostic systems for in-situ structural integrity monitoring have been in progress. Typically, these diagnostic systems may utilize a number of sensory devices that are built in host structures and operate as sensors. As the sensors merely receive diagnostic signals propagating through the structures, the diagnostic systems are referred to as passive systems. Such passive diagnostic systems have difficulties in regional monitoring and adaptive self sensing. The active systems disclosed in U.S. patent applications, Ser. No. 10/942,714, filed on Sept. 16, 2004 and issued as U.S. Pat. No. 7,286,964, Ser. No. 10/942,366, filed on Sept. 16, 2004 and issued as U.S. Pat. No. 7,117,742, Ser. No. 11/304,441, filed on Dec. 14, 2005, and abandoned, Ser. No. 11/397,351, filed on Apr. 3, 2006 and issued as U.S. Pat. No. 7,281,428, Ser. No 11/414,166, filed on Apr. 27, 2006 and issued as U.S. Pat. No. 7,197,931, Ser. No 11/445,452, filed on Jun. 2, 2006 and issued as U.S. Pat. No. 7,246,521, Ser. No 11/502,127, filed on Aug. 9, 2006 and issued as U.S. Pat. No. 7,325,456, and Ser. No. 11/502,319, filed on Aug. 9, 2006 and issued as U.S. Pat. No. 7,322,244, which are incorporated herein by reference in their entirety, may provide enhanced capabilities in regional monitoring and self sensing. In the active systems, one or more of the sensors may generate diagnostic signals that propagate through the host structure, while others may develop sensor signals in response to the diagnostic signals. Hereinafter, the terms patch, sensor, and actuator are used interchangeably as a patch may have capabilities to transmit and/or sense the signals.

As the number of patches in the active systems has increased, the complexity in arranging and operating the patches also has increased. As such, there is a need for a new approach in networking the patches to optimize the use of the patches and to enhance the efficiency and accuracy of the diagnostic system.

SUMMARY OF THE DISCLOSURE

A diagnostic network patch (DNP) system that is attached to a host structure for monitoring the structural conditions thereof is provided. The DNP system contains patches and is capable of detecting and monitoring flaws/damages of the host structure as well as objects around the host structure. Like the nerve system of the human body, the DNP system forms a wave-ray communication network in the host structure by establishing signal paths between actuators and sensors, wherein various types of signals travel through the signal paths.

According to one embodiment, a method of operating an interrogation system that has a plurality of patches attached to an object, each patch being capable of generating a diagnostic wave and/or developing a sensor signal in response to the diagnostic wave, includes steps of: generating an undirected graph that includes a plurality of paths, each path connecting two of the patches; generating a directed graph based on the undirected graph; reconfiguring the directed graph; and scanning the object for an anomaly by use of the directed graph.

These and other advantages and features of the invention will become apparent to those persons skilled in the art upon reading the details of the invention as more fully described below.

DETAILED DESCRIPTION OF THE PREFERRED EMBODIMENTS

Although the following detained description contains many specifics for the purposes of illustration, those of ordinary skill in the art will appreciate that many variations and alterations to the following detains are within the scope of the invention. Accordingly, the following embodiments of the invention are set forth without any loss of generality to, and without imposing limitation upon, the claimed invention.

Figures 1A, 1B:
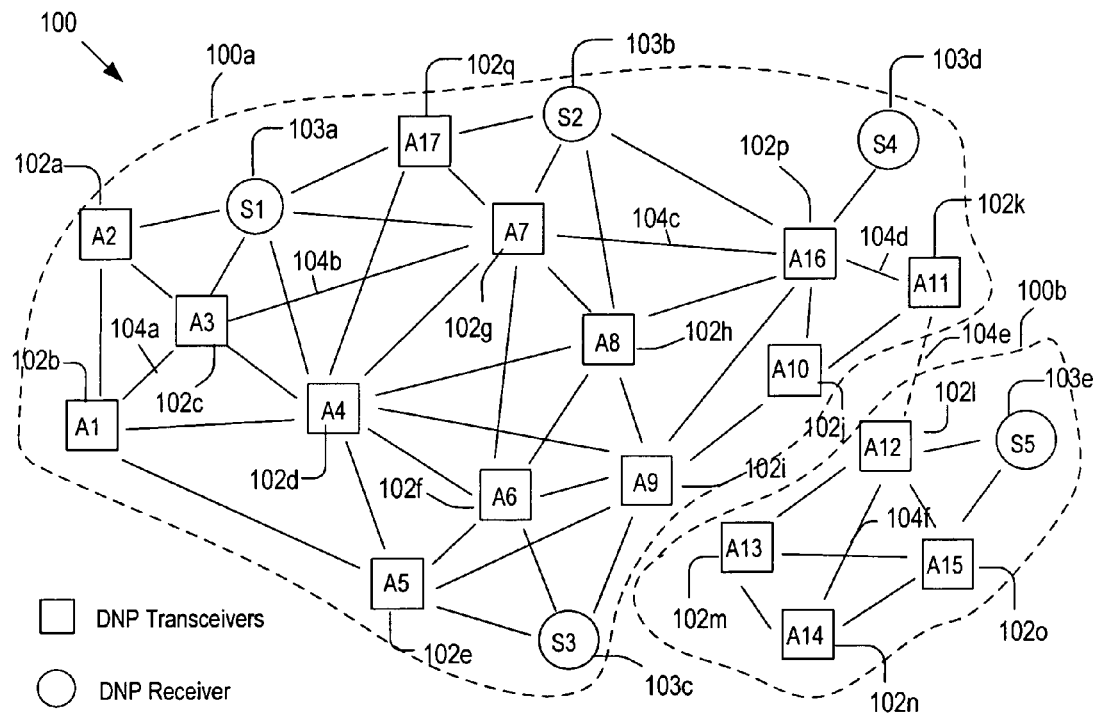
FIG. 1A shows an undirected Euclidean graph for networking patches in accordance with one embodiment.
FIG. 1B shows a directed graph generated by use of the undirected Euclidean graph in FIG. 1A.

FIG. 1A shows an undirected Euclidean graph 100 for networking patches 102 and 103 in accordance with one embodiment. The patches 102 may be transceivers that can generate and/or respond to Lamb waves while the patches 103 may be receivers that can only develop electrical signals in response to the Lamb waves. More detailed description of the patches or nodes 102 and 103 can be found in the previously referenced U.S. patent applications, Ser. No. 10/942,714, filed on Sep. 16, 2004 and issued as U.S. Pat. No. 7,286,964, Ser. No 10/942,366, filed on Sep. 16, 2004 and issued as U.S. Pat. No. 7,117,742, Ser. No 11/304,441, filed on Dec. 14, 2005 and abandoned. Ser. No 11/397,351, filed on Apr. 3. 2006 and issued as U.S. Pat. No. 7,281,428, Ser. No 11/414, 166, filed on Apr. 27, 2006 and issued as U.S. Pat. No. 7,197, 931, Ser. No 11/445,452, filed on Jun. 2, 2006 and issued as U.S. Pat. No. 7,246,521, Ser. No 11/502,127, filed on Aug. 9, 2006 and issued as U.S. Pat. No. 7,325,456, and Ser. No 11/502,319, filed on Aug. 9, 2006 and issued as U.S. Pat. No. 7,322,244. The Euclidean graph 100 may represent the initial network of transmission paths and disclosed in U.S. patent application Ser. No. 10/942,714, which was filed on Sep. 16, 2004 and issued as U.S. Pat. No. 7,286,964, as a diagnostic network patch (DNP) graph of G=(V, E) that consist of a set V of patch nodes and a set E of transmission edges connecting a pair of patch nodes each. The Euclidean graph 100 may be also represented by adjacency matrices or adjacency linked lists. The application also discloses a directed DNP graph that is defined by a list of patch nodes and transmission paths associated with each patch node.

The network graph 100 may be generated, for given transmitters 102a-q and receivers 103a-e, by connecting each patch to other patches within a distance d to form edges or transmission paths 104. The distance d may be the maximum allowable separation between a transmitter and a receiver without losing the integrity of communication therebetween, and affected by the signal-to-noise ratio of the diagnostic wave (such as Lamb wave) and the attenuation of wave intensity by the structural material along the paths. As the distance d increases, the density of the graph 100 decreases. The graph 100 may evolve, i.e., the distance d may be changed to adjust the sensitivity of the graph 100 in detecting damages therein. Hereinafter, the term damages collectively refer to any kinds of physical anomalies in the structure, such as holes, cracks, repair patches, etc. and the local change of temperature and pressure distribution. Without limiting the scope of the present invention, the anomaly can refer physical and motional change of any fixed or movable bodies placed outside of the structure for three dimensional interrogations, wherein the diagnostic wave includes laser, acoustic, electromagnetic, and X-ray beams. Hereinafter, the terms damage and anomaly will be used interchangeably.

FIG. 1B shows a directed graph 105 generated by use of the undirected graph 100 in FIG. 1A. The directed graph or digraph 105 may be generated by assigning to each path one or two arrows 1010 that indicate the directions of diagnostic wave propagation. The graph 105 may include one or more cyclic paths, wherein each cyclic path refers to a closed loop formed by a set of directed arrows 1010. For instance, the patches or nodes A1 106a, A2 106b, A4 106d, A5 106e, and A6 106f may form a cyclic path. The terms cyclic graph and acyclic graph respectively refer to graphs with and without a cyclic path. The graph 105 may be represented by an adjacency matrix (or list) and, in that case, the adjacency matrix may be identical to that of the graph 100. Each adjacency matrix may have ones for the diagonal elements as well as the elements corresponding to the arrows 1010, and zeroes for the other elements. If the graph 105 is weighted, the non-zero matrix elements may have values other than one.

To locate anomalies in the structure, a set of diagnostic waves, such as Lamb waves, may be generated by transceivers 106 in the digraph 105, while the transceivers 106 or receivers 108 may develop sensor signals in response to the waves. Based on the received signal, the undirected graph 100 and/or digraph 105 may be reconfigured to have denser distribution of paths around suspected areas. Also, to maintain the total number of paths below a certain limit, the paths around areas with less likelihood of anomalies may be deleted.

In the undirected graph 100 and digraph 105, each path may be associated with a value called "weight." The weight may be the physical length of the path, time-of-flight for a wave to travel the path, or change in the measured structural condition index (SCI) value of the path due to anomalies. A graph is called non-weighted if each path is presented either one or zero: one if a path between two nodes exists and zero otherwise. For instance, in FIG. 1A, the weight of the path between the nodes A1 102b and A11 102K is zero. A non-weighted graph or digraph may be considered as weighted using two numbers. A route may be defined as a set of paths for connecting one node to another. For instance, in FIG. 1A, a route consisting of the paths 104a-104d may connect the node A1 102b to A11 102k. The weight of a route may be defined as the sum of weights associated with the paths along the route. When the graph 100 or digraph 105 is represented by a matrix, the matrix element (i,k) may correspond to the weight of the path from $i^{th}$ node to $k^{th}$ node.

Depending on the types of weight and whether a graph is undirected or directed, various algorithms may be used to reconfigure the graph 100. For undirected and non-weighted graph 100, a recursive depth-first search (DFS) method may be used. For a given pair of nodes, the weights of all possible routes between the two nodes may be calculated. Then, the route having the minimum weight, referred to as shortest or lowest route, may be deleted from the graph. The step of calculating and deleting shortest routes may be repeated for all possible combinations of the nodes in the graph. The recursive DFS method may also search for bridges 104e connecting the subgraphs 100a, 100b (FIG. 1A), where the bridge is defined as an edge that, if removed, would separate a connected graph 100 into two subgraphs 100a, 100b. The recursive DFS method may be used to represent the graphs 100, 105 as the adjacency matrices. To generate the adjacency matrices, the recursive DFS method may visit a patch node and recursively visit all the adjacent nodes that have not yet been visited. The digraph 105 may be converted into a directed acyclic graph (DAG) 105a by removing back edges, such as 1010d, and thereby breaking the closed loop formed by A1, A2, A6, A4, and A5.

In an undirected and weighted graph, a breadth-first search (BFS) method may be used to find shortest routes. As in the case of DFS method, for a given pair of nodes, the weights of all possible routes between the two nodes may be calculated. Then, the route having the minimum weight, referred to as shortest or lowest route, may be deleted. The step of calculating and deleting shortest routes may be repeated for all possible combinations of the nodes in the graph. The BFS method may also find the maximum-detection single-source path routes connecting a selected patch node to the rest of the nodes in the graph by the use of the full BFS tree rooted at the selected node. Herein, the maximum-detection single-source path route can be defined as the path route, starting from a source patch to any designation patch, that have the maximum route weight of summing the SCI change or anomaly-detection probability of the paths comprised in the route. In addition, the BFS method may obtain the maximum-detection all-pair path routes connecting each pair of nodes, by sorting the SCI values and parent-link tree representations for each node. The maximum-detection all-pair path routes form a set of the routes for any source patch and designation patch such that any route of the set has the maximum route weight of summing the SCI change or anomaly-detection probability of the paths comprised in the route.

For an undirected and weighted graph, a modified minimum spanning tree (MMST) method may be used to reconfigure the graph. A minimum spanning tree in a weighted undirected graph may be defined as a set of edges for connecting a source node to the rest of the nodes and the total weight w(T) has the minimum value, where the total weight w(T) is calculated by the equation: wm=Σw(e) for e⊂E', E'⊂E and where E, E' respectively represent the sets of paths in the entire graph and the minimum spanning tree. The weight w(e) for each path or edge e is a non-negative number. The modified minimum spanning tree (MMST) method may generate two MMSTs: a first tree that has the minimum w(T) and correspond to the minimum spanning tree; and a second tree that has the maximum w(T). Then, a portion of the minimum spanning tree may be deleted from the graph. Boruvaka's algorithm may be used to find the MMSTs of anomaly detection-path distributions based on maximal and minimal total weight of the SCI value change in each path. Kruskal's algorithm may be also used to determine the coverage area for a given patch distribution and the sparsity of the graph by the use of the MMSTs, wherein the distance between patch nodes is used as the weight.

In a directed and weighted graph, referred to as network, a modified shortest-route tree (MSRT) method may be used to reconfigure the network. A single-source MSRT may be considered as an interrogation subnetwork containing a source node and all patch nodes reachable from the source node. The MSRT may be a directed interrogation tree rooted at the source and every route in the tree is a shortest interrogation route. As in the case of the MMST method, two single-source MSRTs (or, shortly MSRTs) may be generated: a first MSRT having the minimum weight; and a second MSRT having the maximum weight. Dijkstra's algorithm or Bellman-Ford's algorithm may be used to find single-source shortest interrogation routes in single-source MSRTs. Upon determination of the first MSRT, a portion of routes in the first MSRT may be deleted. The step of determining and deleting a portion of MSRTs may be repeated for all of the nodes in the network.

The shortest algorithms, which collectively refer to the algorithms used in the DFS, BFS, MMST, and MRST methods, may search the minimum or maximum anomaly-detection routes. The shortest algorithms may determine the source-sink shortest route to find the shortest interrogation route from a source to a sink, single-source shortest routes to find the shortest interrogation routes from the source to the reset of the nodes, and all-pairs shortest routes to find the shortest interrogation route connecting each pair of patch nodes, where the source and sink respectively represent the staring and finishing patch nodes. This interrogation network or weighted diagraph can be represented as a list of transmission-path edges or an adjacency matrix. If transmission paths have negative SCI value weights, the method of searching source-sink longest routes can be limited to acyclic interrogation networks or weighted interrogation directed graphs (digraphs or DAGS). As a variation, Floyd's algorithm may be used to search for the maximum and minimum anomaly-detection routes in a network and thereby generate all shortest interrogation routes. If physical length is used as the weight, the diameter of a Euclidean network may be specified by the largest element of an all-shortest-routes matrix. If the diameter is larger than a preset limit, the Euclidean network may be divided into two or more graphs.

Upon deleting paths around areas with less likelihood of anomalies, additional paths may be added to the graph to reconfigure the graph. In general, the routes around anomalies may have higher SCI value changes than those remote from the anomalies. To enhance the resolution around the suspected areas, the additional paths may be connected to or positioned adjacent to the nodes having high SCI value changes. Subsequently, a reconfigured directed graph may be generated and the reconfiguration process may be repeated until the locations of anomalies are determined within an intended accuracy.

Prior to the step of adding paths to the graph, reachability between patch nodes 102 may be checked as an optional step. To verify the reachability of transmission paths 104 between the patch nodes 102, a transitive closure that has transmission-path edges from a patch node to the rest of the patch nodes reachable from that node may be computed. The transitive closure can be computed by constructing an adjacency matrix with self loops for every patch node and computing the adjacency-matrix power. Either Warshall's algorithm or DFS-based transitive-closure algorithm may be used to determine the transitive closure.

To find whether the digraph 105 has large cycles or cyclic routes, the patch nodes of the diagraph may be divided into strong components that are interrogation digraphs and include mutually reachable patch nodes for every patch node. Kosaraju's algorithm may be used to compute the strong components by assigning a component number to each patch node in a node-indexed array. As a variation, other methods such as Tarjan's algorithm or Gabow's algorithm may be used to compute the strong components. For given strong components of an interrogation digraph (DAG), a kernel of the DAG may be built, wherein the kernel of the DAG may be a set of directed transmission-path edges that go from one component to another. Then, the transitive closure of the kernel of the DAG may be computed.

Scheduling the sequence of transmission paths may be performed by topologically sorting an interrogation DAG. In the topological sort, an embodiment of the present disclosure maintains a queue or node-indexed array of source patches and uses a table that keeps track of the in-degree entries of each patch node in the DAG. When the embodiment removes a source patch from the queue and label it, the in-degree entries corresponding to each of the nodes on its adjacency list may be decreased whereas the patch nodes that have not been removed from the queue induce the DAG. Thus, patch nodes may come off the queue in a topologically sorted order.

In some cases, the anomaly may change over time. To detect the variation of the anomaly over time, an interrogation network may be discriminated into a set of networks according to a given set of weight values. For a network containing negative weights, Bellman-Ford algorithm or Floyd's algorithm may be used to determine all-pairs shortest routes. The process of discrimination may be performed at various points in time, and at each point in time, the interrogation network is discriminated into a set of networks corresponding to the set of weight levels. Then, for each of the discriminated network, all-pairs shortest routes may be determined.

By comparing the all-pairs shortest routes of the discriminated networks with each other, the variation of an anomaly over time may be obtained.

Figure 2A:
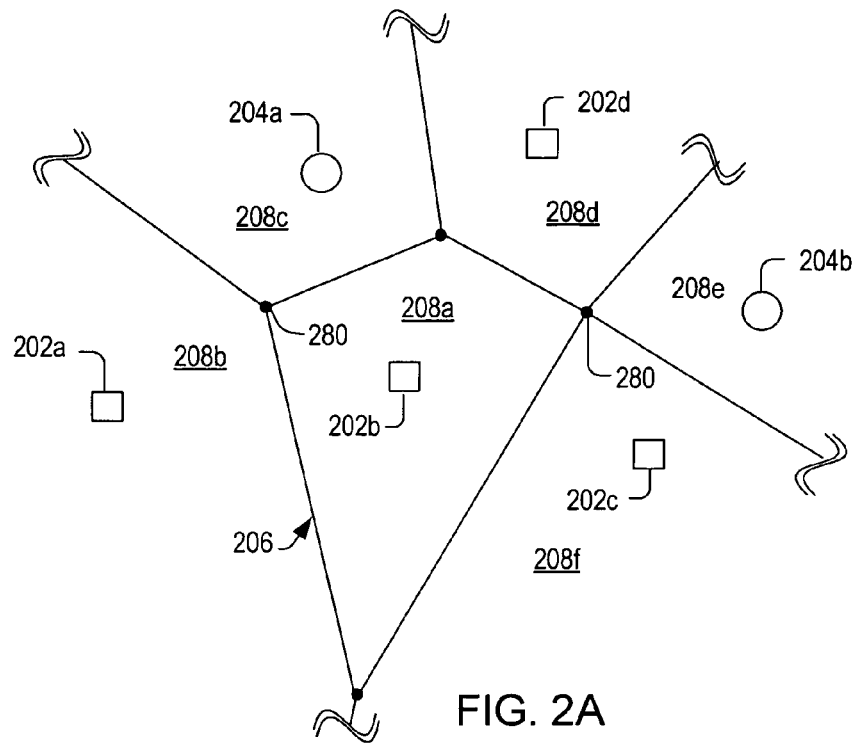
FIG. 2A shows a Voroni diagram for arranging patches to form the undirected graph in FIG. 1A.

DNP patches may be distributed randomly or in a pattern, such as mesh-grid or pentagonal shape, as explained in the previously referenced application, U.S. patent application, Ser. No. 10/942,366, which was filed on Sep. 16, 2004 and issued as U.S. Pat. No. 7,117,742. FIG. 2A shows a Voroni diagram 206 for arranging the patches 202 in a structure. The patches 202 may include transmitters 202a-d and receivers 204a-b. Each of the regions 208a-f may correspond to one of the patch nodes of 202a-d and 204a-b and all the points in one region, say 208a, are closer to the patch node 202b than any other patch node. The diagnostic patches of 202a-d and 204a-b may be distributed on a geometric plane according to the Voroni diagram 206 that is generated by use of a randomized incremental algorithm, a divide-and-conquer algorithm, or a plane sweep algorithm. Each line segment of the Voroni diagram 206 may bisect an edge and have ends referred to as Voroni node points 280. Alternatively, various types of algorithms, such as 2D binary tree search, near neighbor search, and 2D-grid range search algorithms, may be used to perform the operations of searching, inserting, and deleting the diagnostic patches 202a-d, 204a-b.

Figure 2B:
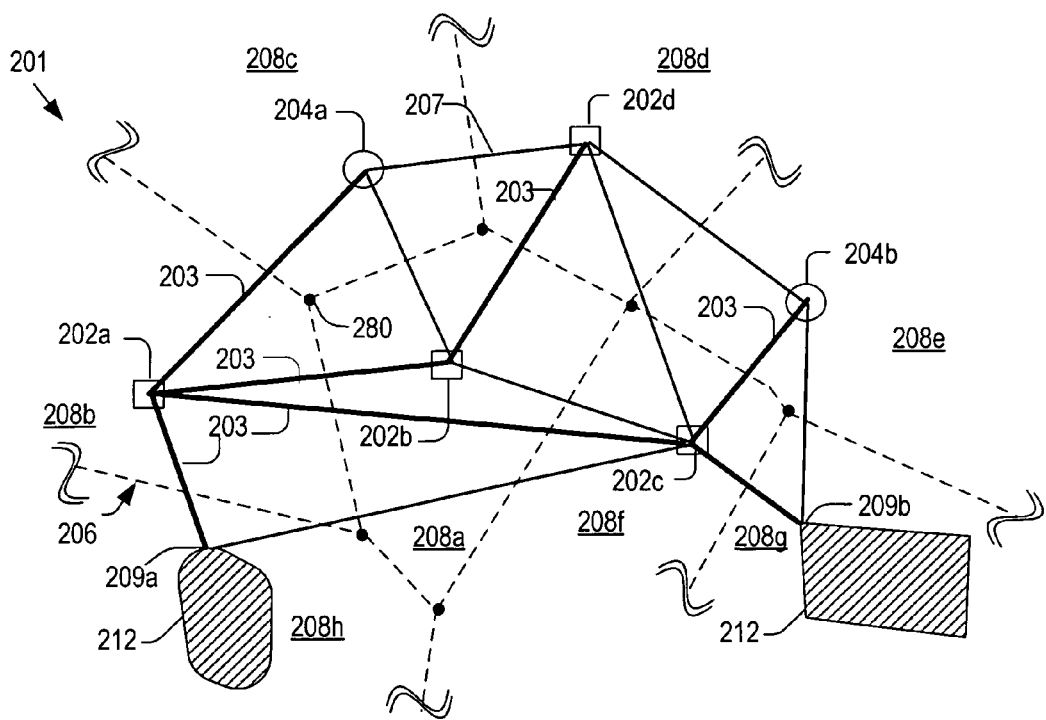
FIG. 2B shows Delaunay triangles associated with the Voroni diagram in FIG. 2A.

FIG. 2B shows a Delaunay triangle (DT) diagram 201 generated by use of a Voroni diagram as shown in FIG. 2A. As depicted, each Delaunay triangle may be determined by three neighboring nodes, such as 202a, 204a and 202b, for instance. In some cases, the structure may include obstacles 212, such as irregular boundaries, holes, or structural joints, which the diagnostic waves cannot propagate through or are extremely distorted by. In such cases, Delaunay triangulation may generate Delaunay triangles by connecting obstacle vertices 209a-209b as well as the patch nodes 202. Each of the edges 203, 207 may be a convex dual of the Voroni diagram 206 and form a Lame-wave transmission path in a diagnostic network system. The triangulation is locally equiangular if, for every convex quadrilateral formed by triangles 204a-202b-202a and 204a-202b-202d that share common path of 204a-202b, the minimum internal angle of the triangles 204a-202b-202a and 204a-202b-202d is at least as large as the minimum internal angle of triangles 204a-202d-202a and 202b-202d-202a. A Delaunay triangulation may be locally equiangular triangulation for convex quadrilaterals formed by the patch node and neighbors. To generate a DT diagram 201, each patch node of 202a-d, 204a-b and 209a-b maintains a neighborhood table which contains its neighbors in the DT graph 201. The DT table corresponding to each patch node contains the information of the coordinates and identification numbers of its DT neighbors. One embodiment of the present disclosure may test patch nodes neighboring on a patch node about whether these neighboring patch nodes can be candidates of the DT neighbor of the patch node by verifying the locally equiangular for convex quadrilaterals formed by the patch node and neighbors. It is determined whether or not the patch nodes adjacent to a selected node can be candidates of the DT neighbor patch nodes. To interactively edit the network configuration, each patch node can provide its DT neighbor nodes' information in the DT table, such as coordinates and identification number of a transmitter, and the information of clockwise and counter-clockwise DT neighbors with respect to the receiver.

The DT diagram 201 may be a planar graph and contain a set of edges 203 forming a Euclidean minimum spanning tree (EMST). The EMST 203 includes a set of shortest edge lines connecting a given set of the node points together.

The EMST 203 may include edges or paths formed by connecting every pair of patch points 202a-d, 204a-b, 209a-b within a distance d. The EMST 203 may be generated by dividing the plane of diagnostic area into squares that contain about log N/2 patches each, connecting the squares by straight lines shorter than the distance d, and including only the edges connecting each patch to the patches in the neighboring squares. For the graph searching, one embodiment of the present disclosure may utilize Kruskal's algorithm or take the interrogation graph 201 through implementing the priority-first-search (PFS) of Prim's algorithm that uses a priority queue with the remove-the-minimum operation.

Figure 3:
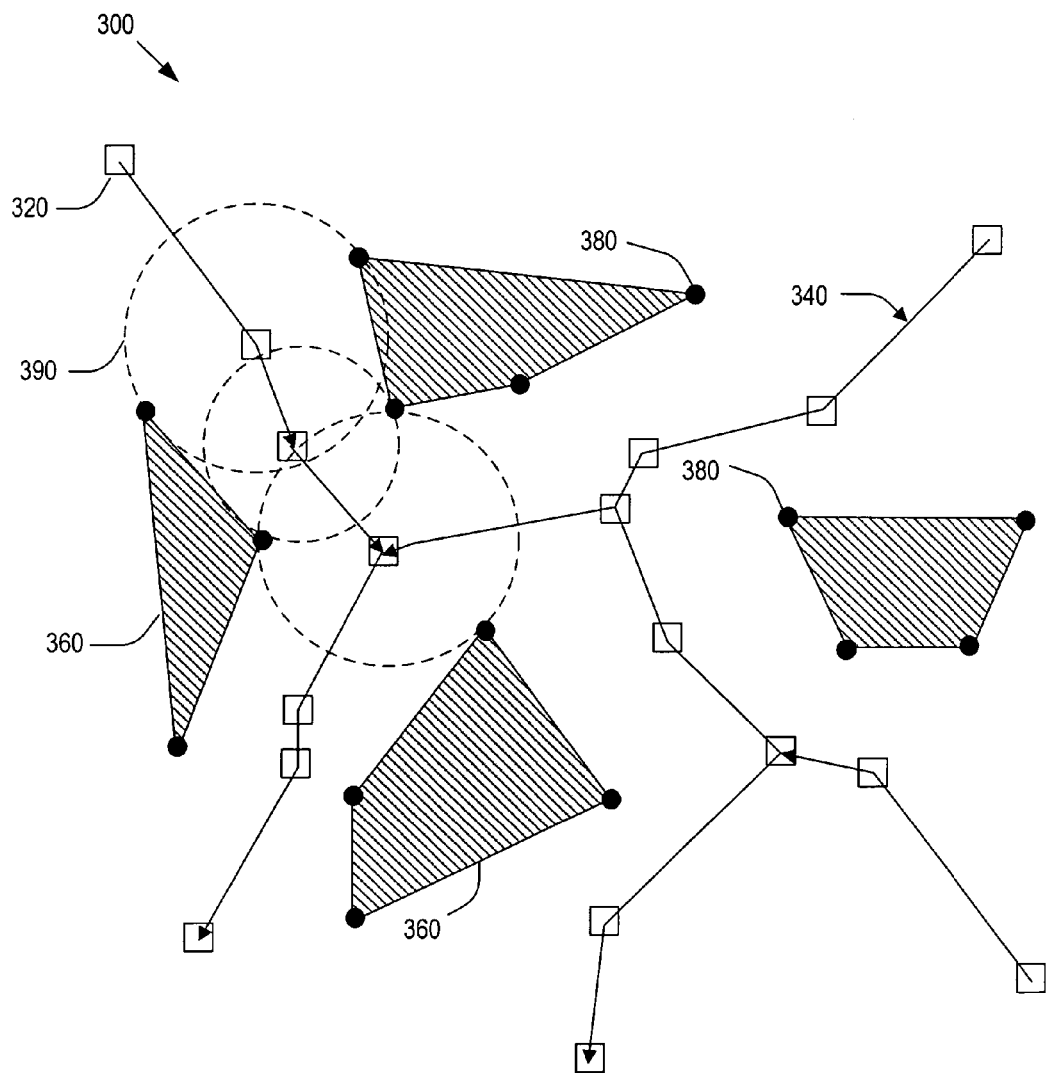
FIG. 3 shows shortest interrogation routes formed in a structure having obstacles in accordance with another embodiment.

As discussed above, the Voroni diagram 206 may be used to optimize patch distribution in a host structure that has obstacles such as irregular boundaries, holes and structural joints (or 3-dim obstacles, such as cubes, cylinders, polyhedrons). FIG. 3 shows shortest interrogation routes 340 between patches in a structure having polygonal obstacles (or polyhedrons) 360 in accordance with another embodiment. Dijkstra's algorithm may be used to distribute patches 320 along a shortest interrogation route 340. Since the obstacles 360 may have irregular shapes, the vertices of polygonal obstacles (or, polyhedrons) may be considered as node point 380 in generating a Voroni diagram. Subsequently, all edges intersecting the obstacles may be removed from the diagram. For a given set of obstacles and set of patches in the structure, an interrogation visibility graph 300 may be generated by forming a Voroni diagram and thence removing paths that pass through the obstacles 360.

To establish routes that extend between obstacles 360, a method of placing the patches 320 on passable channels may be used. The passable channels or routes may be the lines connecting the points of a Voroni diagram within the circles 390, wherein each circle may pass through two obstacle nodes and have a radius to include only one of the patches therein. The patches 320 may be placed to form shortest interrogation routes 340 of the interrogation graph. The shortest interrogation routes may be found by graph search methods.

Figure 4:
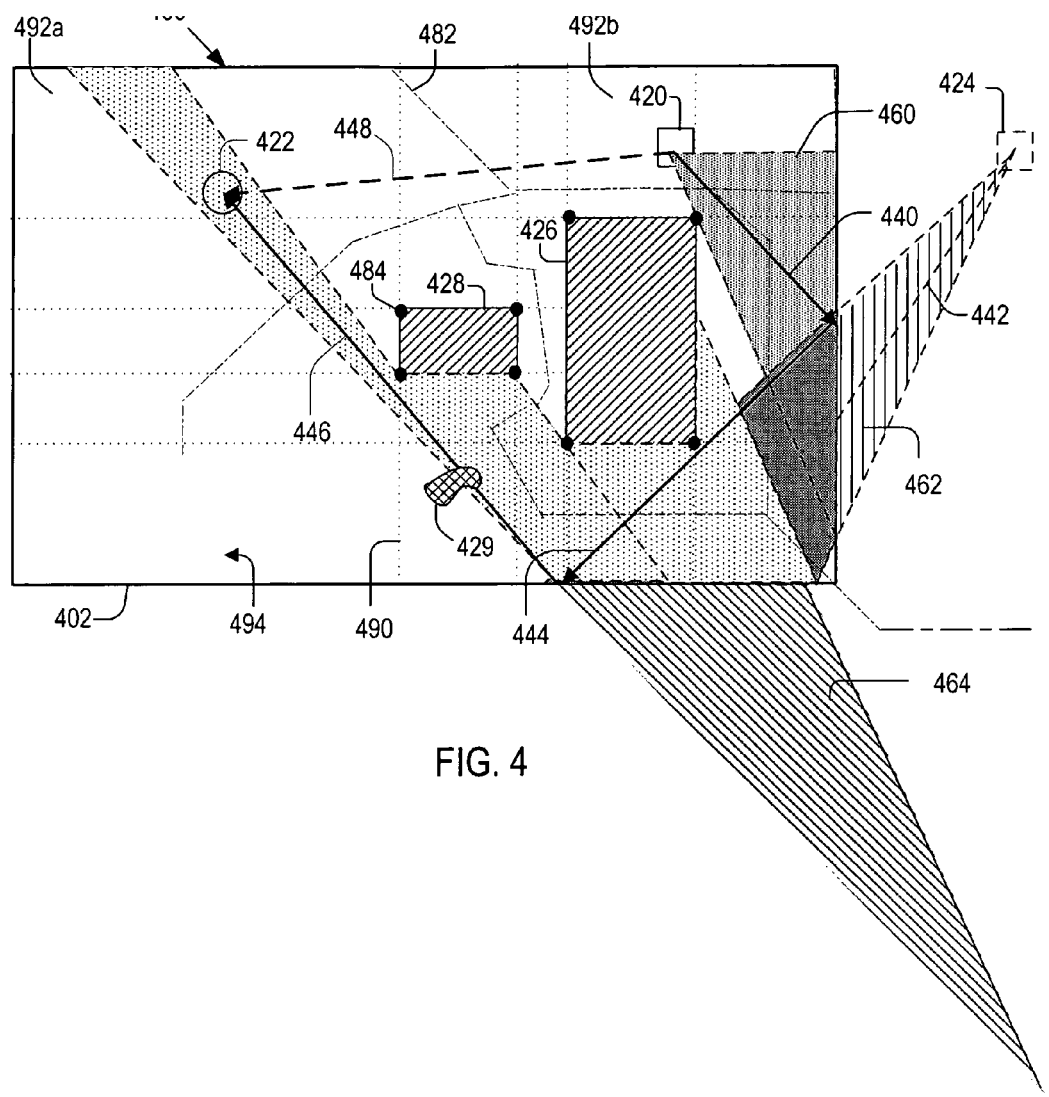
FIG. 4 shows a signal route formed around an obstacle in accordance with another embodiment.

FIG. 4 shows a signal route between two patches 420 and 422 in accordance with another embodiment. As depicted, the structure 400 may have a rectangular or cubical boundary 402 and two obstacles 426, 428 with vertices 484 therein. The interrogation signal transmission lines 448, 440, 444, 446 may be formed between the DNP actuator or signal transmitter 420 and a DNP sensor 422 attached to structure 400. For computing the wave propagation through the interrogation transmission paths of 440, 444, 446, an image source method based on beam tracing or ray tracing technique may be used. In FIG. 4, the lines 482 represent a Voroni diagram.

The image source method may generate a specular reflection path 442 by considering a virtual actuator 424 that is a mirror image of the real interrogation actuator 420 with respect to a polygonal line (or polyhedral surface) of the structural boundary 402. For the virtual actuator 424, a specular reflection path 442 can be constructed by varying the incidence angle with respect to the bottom boundary until the reflected line segment hits the sensor 422. Specular reflection paths may be computed up to any order by recursively generating virtual actuators 424. A ray tracing method may find propagation paths between the actuator 420 and the sensor 422 by generating rays 440, 444, 446 emanating from the actuator position and following them through the structural obstacles 426, 428 or boundaries until a set of rays that reach the sensor is found. A beam tracing method may classify propagation paths from an actuator by recursively tracing beams through the structural obstacles or boundaries. For each beam, polygons (or polyhedrons) 460, 462, 464 in the boundaries may be considered for intersection with the beam in front-to-back visibility order. As intersection polygons (or polyhedrons) 460, 462, 464 are generated, the original beam is clipped to remove the shadow region. Then, a transmission triangle is constructed matching the shadow region. Finally, a reflection beam 446 is constructed by mirroring the transmission beam over the polygon lines (or polyhedral surfaces).

One embodiment may decompose two (or three) dimensional structural geometry for a spatial subdivision and store it in a data structure such that the 2D (or 3D) geometric space can be partitioned into rectangles 494 (or cube) whose boundaries 490 are aligned with lines (or plane) of structural boundaries 402 and such that rectangle (or cube) adjacencies are encoded in a data structure enabling efficient traversals of 2D (or 3D) space during the later beam tracing phase. The embodiment may build a data structure of rectangles (or cubes) which store topological adjacencies associated with vertices and edges by using a binary space partition algorithm, and perform a recursive binary split such that a 2D (or 3D) space is split into rectangles (or cubes) separated by lines (or surfaces).

After the spatial subdivision has been constructed, the embodiment may determine triangles 460, 462, 464 that represent the regions reachable from each actuator by different sequences of reflections and transmissions. The beams may be traced from each actuator via a best-first traversal of the rectangle (or cube) adjacency graph starting in the rectangle 492b (or cube) containing the actuator. When the embodiment may traverse a rectangle 494 into a new rectangle (or cube), a copy of current triangular (or conical) beam is clipped to include only the region passing through rectangular obstacles 426, 428 to model transmission. Each line 490 may be an extension of a boundary of rectangular obstacles 426, 428. At each line 490, a copy of the transmission beam 440 may be mirrored across the line (or plane) supporting the rectangular (or cubical) boundary 402 to model specular reflections 462. The traversal along any sequence may terminate when either the length of the shortest path within the beam or the cumulative attenuation exceed some specified thresholds. Finally, the beams are queried using beam tree data structure to compute propagation paths to specific sensor locations.

When the patch locations are adjusted so as to rearrange the patches in the host structure, precomputed beam trees may be used to identify propagation sequences of transmissions and reflections potentially reaching the sensor location. The potential propagation sequences may be enumerated by finding all the beams containing the location of the sensor 422 since every beam contains all points potentially reachable by rays traveling along a particular propagation sequence. Specifically, a rectangle (or cube) 492a containing the sensor 422 may be found by searching binary space partition 490. Then, each beam tree node associated with that rectangle 494 may be checked to determine whether the beam stored in the beam tree node contains the sensor 422. If it does, a potential propagation sequence for the actuator 420 and sensor 422 has been found, and the ancestors of this beam tree node encode the set of reflections and transmissions through the boundaries of the rectangle subdivision 494 that a ray must traverse from the actuator 420 to the sensor 422 along this sequence. For each propagation sequence, the propagation path including line segments 440, 444 and 446 may be constructed. The propagation path including line segments 440, 444 and 446 may represent the trajectory of a light emitted from the patch 420 and reflected at the boundary 402 of the structure 400.

Figure 5:
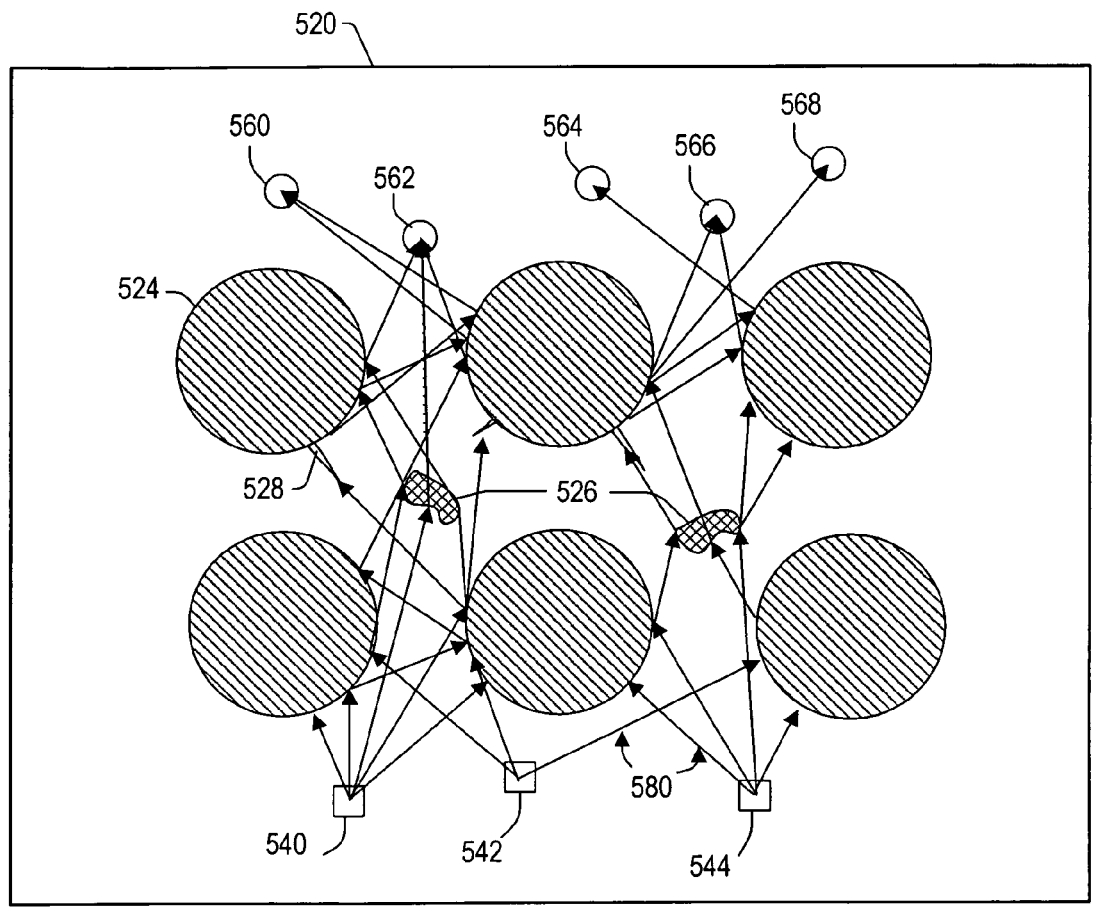
FIG. 5 shows signal routes formed in a structure having circular obstacles in accordance with another embodiment.

FIG. 5 shows signal routes between multiple patches 540, 542, 544, 560, 562, 564, 566, 568 with circular obstacles 524 disposed therebetween in accordance with another embodiment. As depicted, the structure 520 may have circular obstacles 524, cracks 528 as well as anomalies 526. A computational geometric ray mirror method may be used to construct wave propagation paths 580. The ray mirror method may compute reflection paths in the structure 520 by mirroring incidence paths along the line normal to the boundaries of the circular (or cylindrical) obstacles 524. It may also use a graph-based data structure to store a propagation ray tree and geometric subdivision of binary space partition.

The previous embodiments disclosed in the parent application include a decomposition method for extracting interrogation signals from measured Lamb waves and analysis methods to retrieve structural condition index (SCI), such as delay in arrival time, the amplitude and energy of each wavepacket of decomposed signals. The previous embodiments include the methods to compensate the SCI values by using the normality constant of the probability distribution of SCI values in a diagnostic network. Without limiting the scope of the present invention, when the embodiment may use laser, acoustic, electromagnetic, and X-ray beam as a transmission signal for three dimensional interrogation, SCI values can also be delay in arrival time, the amplitude and energy of each wave-packet of decomposed signals, such as laser intensity, flight time of acoustic wave, X-ray absorption. As the distance of a signal transmission path increases, the signal attenuation also increases. In some cases, the degree of attenuation may become so significant that clarifying the SCI value difference between two attenuated signals obtained in the same transmission path may not be feasible. The attenuation of SCI values may be compensated based on the Lamb-wave propagation distance for all interrogation paths in Euclidian networks. For instance, an embodiment may compensate a received wave signal by $v_c(x_s)=\exp(\beta l_s)v_m(x_s)$ for a transmission path, where $v_c(x_s)$ is the compensated signal of each wave packet. The compensation factor $\beta$ may be determined by the average value of $$\beta_{ij} = \frac{1}{l_i - l_j} \log\left(\frac{v_m(x_j)}{v_m(x_i)}\right),$$

where $v_m(x_{i,j})$ is the measured Lamb wave signal at the sensor locating at $x_{i,j}$ with wave propagation distance $l_{i,j}$ apart from the actuator. An embodiment may compensate the delay in time-of-flight and the SCI values by simply multiplying the measured signal with the root of distance $\sqrt{l_i}$ between the actuator and the sensor.

Figure 6:
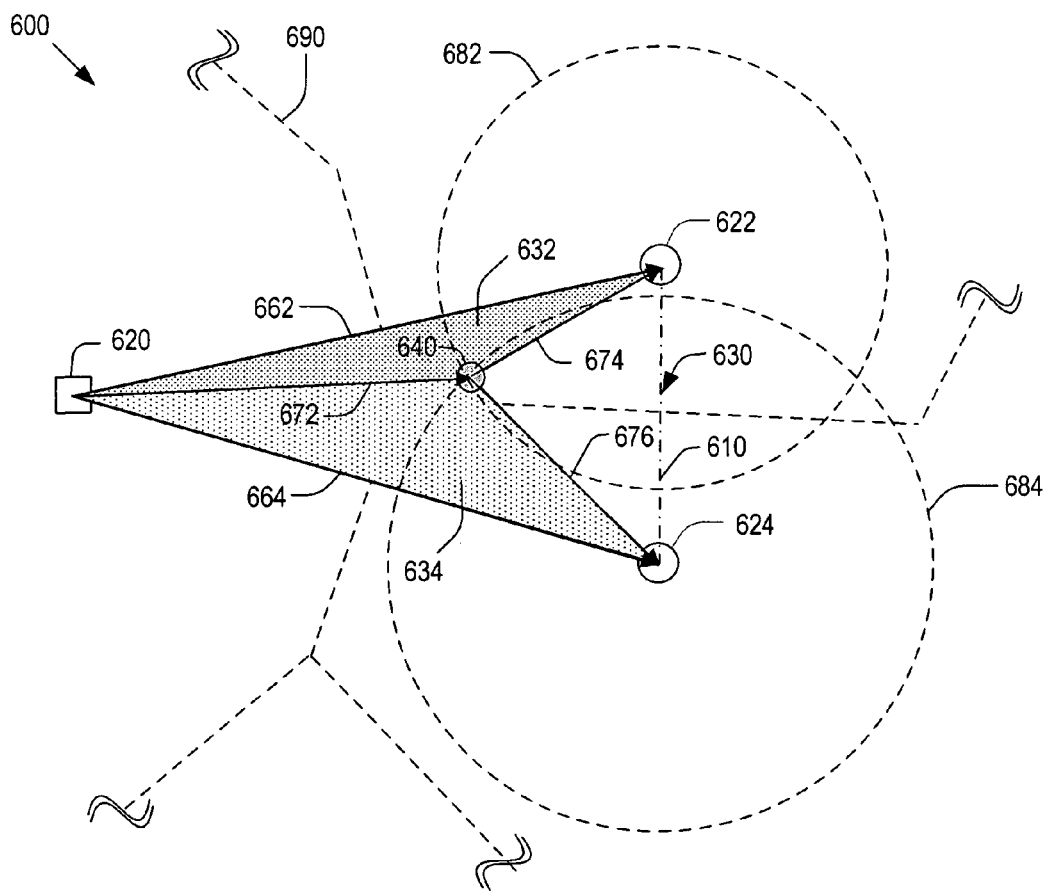
FIG. 6 illustrates locating an anomaly by use of two echo-locating triangles and two influence circles associated with a Delaunay triangle as shown in FIG. 2B.

FIG. 6 illustrates determining the location of an anomaly 640 in a Euclidian interrogation network 600 by use of echo-locating triangulation and two influence circles (or spheres) 682, 684 associated with a Delaunay triangle 630. As depicted in FIG. 2B, the Delaunay triangle 630 may include two transmission paths 662, 664 and a line 610 connecting the two sensors 662, 624. The Delaunay triangle 630 may be determined by a Voroni diagram 690 in a Euclidian interrogation network 600. The echo-locating triangles (ET) 632 and 634 may respectively have the transmission paths 662, 664 as base sides and a common side that corresponds to a line 672 from the actuator 620 to the anomaly 640. The Delaunay triangle 630 is likely to contain a possible existence of the anomaly 640. The location of the anomaly 640 may be determined by the relativity of interrogation distances in the Delaunay triangle 630, and the influence circles 682, 684 of the distances. The diagnostic signal transmitted from the transmitter patch 620 along the line 672 may be scattered by the anomaly 640. Then, the scattered signals may propagate toward the sensors 622, 624 along the paths 674 and 676, respectively. The anomaly 640 may be determined to be at the intersection of influence circles (or sphere) 682, 684. Each influence circle (or sphere) may be represented by $\|x^{damage} - x_j^{sensor}\| = l_{ij} - ct_{ij}^{delay}$, wherein $l_{ij}$ is the distance between the $i^{th}$ actuator and $j^{th}$ sensor, $x_j^{sensor}$ is the coordinate of the $j^{th}$ sensor; the radius of the circle (or sphere), $l_{ij} - ct_{ij}^{delay}$, is a transmission distance 674, 676; and $t_{ij}^{delay}$ is the delay in time, caused by the anomaly 640, for a diagnostic wave to travel the path between the $i^{th}$ actuator and $j^{th}$ sensor. Here c is the average speed of each interrogation wave $c_{ij} = l_{ij}/t_{ij}$ along the interrogation path between the $i^{th}$ actuator and $j^{th}$ sensor. For the case of 3-dimensional interrogation, the plane of ET triangles can be slanted from the normal plane of structure surface.

It is noted that influence circles 682 are used to determine the location of anomaly when the interrogation system covers a two dimensional area. For interrogation systems that cover a three dimensional space, influence sphere are used in place of circles. As such, hereinafter, the term influence circle collectively refers to both influence circles and spheres.

As depicted in FIG. 6, the method of circle (or sphere)-of-influence graph may determine the intersection 640 of the influence circles 682, 684 associated with the DT 630. The method of circle (or sphere)-of-influence graph may determine the anomaly location $(x^d, y^d)$ by simply drawing two influence circles (or sphere) of 682, 684 with the centers at two sensor locations 622, 624 and the radii corresponding to the relative distances 674, 676 of their transmission paths. The damage location may be also determined by solving only two nonlinear equations $(x^d - x_{1,2}^s)^2 + (y^d - y_{1,2}^s)^2 = r_{1,2}^2$, where $r_{1,2} = (l_{1,2} - ct_{1,2})$, instead of solving three nonlinear equations to take an additional path into consideration. If the interrogation signals in the DT 630 have no time delay in the transmission paths 662, 664, damage location 640 will be same as the location of actuator 620. An embodiment may allow the anomaly location 640 to have a value that indicates the degree or strength of the anomaly 640. An embodiment may measure the SCI values E1, E2 and SCI value changes ΔE1, ΔE2 at the sensors 622, 624. Then, the degree D of anomaly may be expressed by an equation $D = (r_1 * \Delta E1 + r_2 * \Delta E2)/(L_1 * E1 + L_2 * E2)$, wherein $r_1$, $r_2$, $L_1$, and $L_2$ are the lengths of edges 674, 676, 662 and 664, respectively. As a variation, the degree D may be calculated by an alternative equation $D = (r_1^{1/2} * \Delta E1 + r_2^{1/2} * \Delta E2)/(L_1^{1/2} * E1 + L_2^{1/2} * E2)$. As another variation, an equation $D = (\exp(\beta_1 r_1) * \Delta E1 + \exp(\beta_2 r_2) * \Delta E2)/(\exp(\beta_1 L_1) * E1 + \exp(\beta_2 L_2) * E2)$, may be used, wherein $\beta_1$, $\beta_1$ respectively represent the compensation factors for the edges 662, 664, as discussed above. Hereinafter, the quantities, r, L, $r^{1/2}$, $L^{1/2}$, β are collectively referred to as compensation factors. Also, the numerators of the three equations for calculating the degree D are referred to as compensated SCI value changes and the denominators of the three equations are referred to as compensated SCI values.

Figure 7:
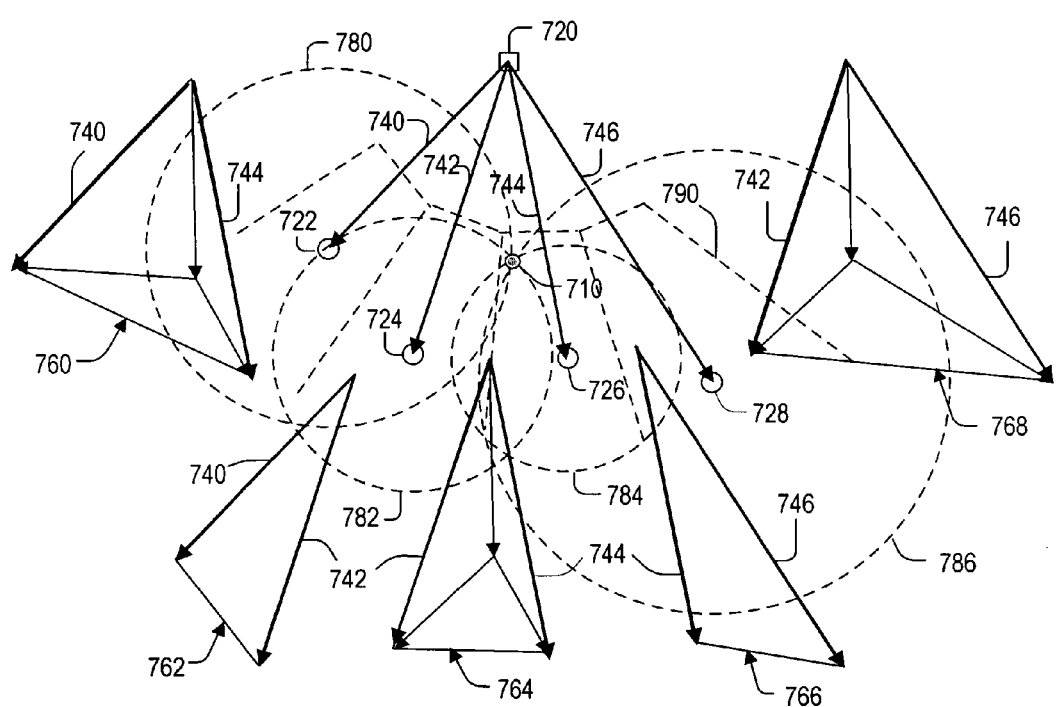
FIG. 7 illustrates determining the location of an anomaly by use of echo-locating triangles and influence circles associated with multiple Delaunay triangles as shown in FIG. 2B.

FIG. 7 illustrates locating an anomaly by use of echo-locating triangles and influence circles (or spheres) associated with multiple Delaunay triangles. As depicted, by overlapping ETs associated with multiple Delaunay triangles 760, 762, 764, 766, and 768, accuracy in determining the location of an anomaly 710 may be enhanced. A diagnostic wave transmitted from a transmitter patch 720 may be scattered by the anomaly 710 and received by the four sensors 722, 724, 7246, and 728. The four sensors may also receive diagnostic waves directly from the transmitter 720 via the paths 740, 742, 744, and 746, respectively. As discussed in conjunction with FIG. 6, the location of the anomaly 710 may be the intersection of the four influence circles (or spheres), 780, 782, 784, and 786. It is noted that the two Delaunay triangles 762 and 746 may not include the anomaly 720 therein and, as a consequence, may not generate any influence circle. In general, an anomaly may be determined by n number of Delaunay triangles. To determine the anomaly location with n Delaunay triangles, an embodiment may make a formulation of finding the location with the n triples $(x_i^s, y_i^s, r_i^s)$ for the given n number of influence circles, satisfying $(x_i^s - x_j^s)^2 + (y_i^s - y_j^s)^2 \leq (r_i^2 + r_j^2)$, $(i,j) \in I_1$ and $(x_i^s - x_j^s)^2 + (y_i^s - y_j^s)^2 \geq r_i^2$, $(i,j) \in I_2$, $x_i^s \geq 1$, $y_i^s \geq 1$, $r_i^s \geq 1$, $i \in I_0$, where the index sets are $I_0 := \{i | 1 \leq i \leq n\}$; $I_1 := \{(i,j) | 1 \leq i \leq n; i < j\}$; $I_2 := \{(i,j) | 1 \leq i \leq n; j \neq i\}$. The formulation may be transformed into an optimization problem by requiring the influence circles (or spheres) to be close to one another such that $$\min \sum_{i \in I_1} (x_i^s - x_j^s)^2 + (y_i^s - y_j^s)^2$$

is obtained. For 3-dim location problem, $$\min \sum_{i \in I_1} (x_i^s - x_j^s)^2 + (y_i^s - y_j^s)^2 + (z_i^s - z_j^s)^2$$

may be obtained. The optimization problem may be solved by using a conventional optimization algorithm.

Figure 8:
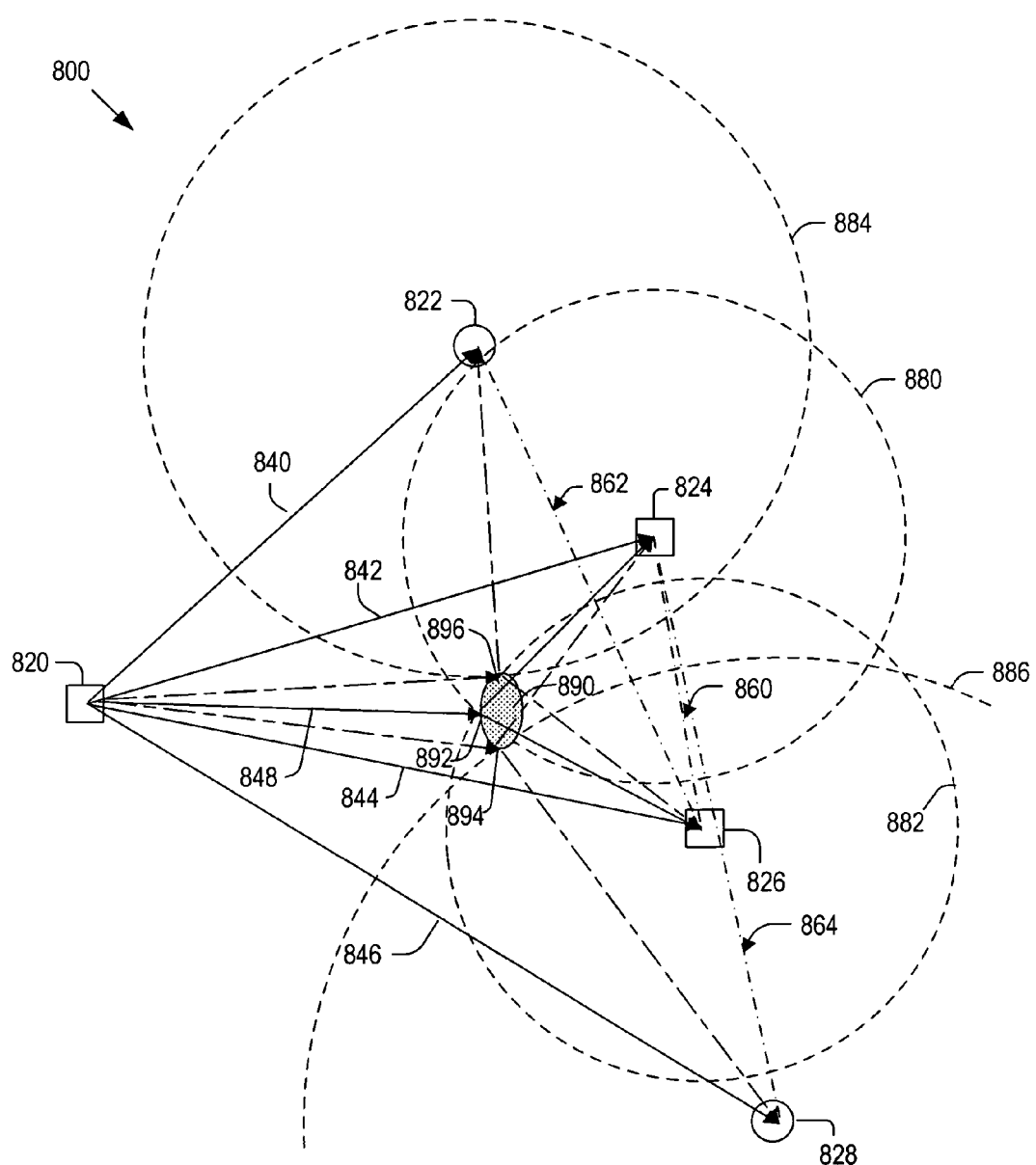
FIG. 8 illustrates determining the shape of an anomaly by use of multiple Delaunay triangles as shown in FIG. 2B.

In general, an anomaly may have a finite dimension as shown in FIG. 8. FIG. 8 illustrates determining the shape of the anomaly 890 by use of multiple Delaunay triangles or ETs. Diagnostic signals from a transmitter 820 may be received by one or more sensors 822, 828 and one or more transceivers 824, 826. Each sensor or transceiver may receive a diagnostic signal directly from the common transceiver 820 and one or more diagnostic signals scattered at various points on the boundary of the anomaly 890. To determine the shape of the anomaly 890, an embodiment may first locate the anomaly 890 by using the inner most DT 860 containing the smallest wedge angle of 842-820-844 among multiple DTs 860-864, and then executes locating anomaly 890 by recursively constructing subsequent DTs 862, 864 with two order neighboring sensors 822, 828 expanding outside from the sensors 824, 826 of the inner DT 860. Thus an embodiment can determine the anomaly shape by projecting the location points 892, 894, 896 computed from each ET, normal to the centerline 848 of the inner most DT 860.

It is noted that the points 892, 894, 896 may be located on the boundary of the anomaly, wherein the boundary faces the transceiver 820. By selecting the transceiver 824 as a transmitter and repeating the similar process as discussed above, the shape of the boundary facing the transceiver 824 may determined. In general, the entire shape of an anomaly may be determined by use of multiple transmitters located around the anomaly.

Figure 9:
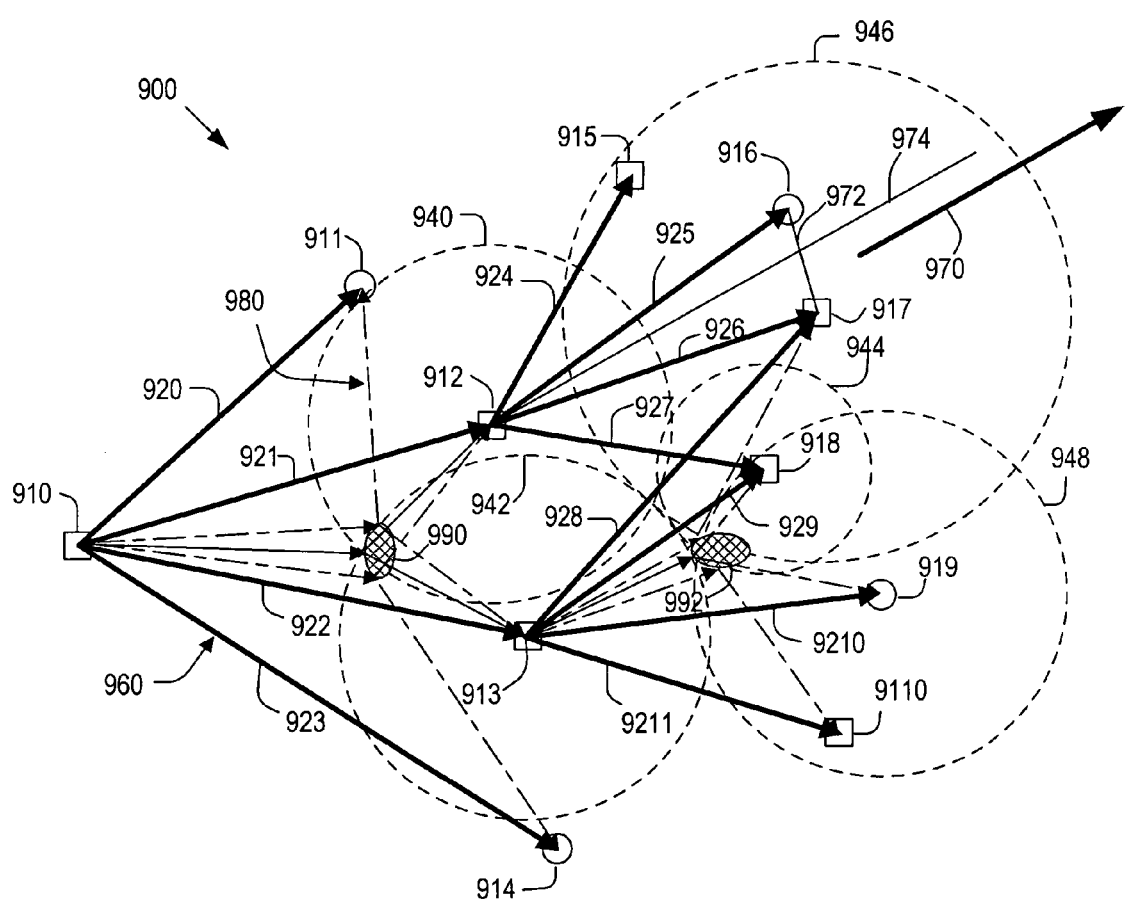
FIG. 9 illustrates progressively determining the locations of distributed anomalies by use of a directional Euclidian shortest-route tree (ESRT) formed in a directed graph as shown in FIG. 2B.

FIG. 9 illustrates progressively locating distributed anomalies 990, 992 by use of a directional Euclidian shortest-route tree (ESRT) 960. For progressive interrogation, a spanning tree 960 in a Euclidian interrogation network 900 may be formed by designating a starting transceiver or source 910 and branching at each node that corresponds to a transceiver. The leaves or leaf nodes of the spanning tree 960 may be sensors, such as sensors 911, 914, 916, and 919. An embodiment may recursively construct ET triangles 980 on the spanning tree 960 of the Euclidian interrogation network 900, and then locate anomalies 990, 992 as explained in conjunction with FIG. 8.

The ESRT 960 may be generated by a priority-first-search (PFS) algorithm that takes the distance to the destination in account when checking the inequality test as it computes shortest routes. As a variation, Dijkstra's algorithm may be used in place of the PFS algorithm. The ESRT tree 960 may be a subnetwork containing the source patch 910 and all patches 911-9110 reachable for the source that forms a directed tree rooted at the source 910 such that every tree route is a shortest route in a network. When Dijkstra's algorithm searches the Euclidian shortest routes towards a destination node, the search may be restricted to nodes within an ellipse (or oval) around the route, rather than the circle (or sphere) centered at nodes.

Upon generation of an ESRT 960, an embodiment may construct a tuple of ET triangle 980 at each of ESRT parent nodes 910, 912 and 913 with the neighboring paths 920, 923, 924, 927, 928, 9211 of the corresponding ESRT path 921, 922, 925, 926, 929 and 9210. Starting from the root node 910, an embodiment may recursively construct the tuples of ET triangles 980 at parent nodes 910, 912 and 913 until it reaches the leaf nodes 916, 917, 918, 919 of the ESRT 960. Then, at each parent nodes 910, 912 and 913 of the ESRT 960, an embodiment may determine an anomaly location by solving the local optimization problem or the nonlinear geometric equations of circle (or sphere)-of-influence graph 940-948, as explained in conjunction with FIG. 6. Then an embodiment may determine the shape of the anomaly by centralizing the ETs 980 of the tuple along the ESRT edge such that an array of the anomaly locations are determined in each ET tuple. Hereinafter, the term centralizing refers to selecting DTs that are approximately aligned in a mean direction. Centralizing may start with calculating the average of the angles between a predetermined direction and the edges of the ESRT, wherein the mean direction has the average angle with respect to the predetermined direction. Then, it is determined if a line (or plane) passing through the actuator of each DT crosses the base of the DT. For the purpose of illustration, the arrow 970 may represent the mean direction of the ESRT 960. The base 972 of the DT formed by 916-912-917 may cross the line (or plane) 974 passing through the actuator 912, wherein the line (or plane) 974 is parallel to the arrow 970. Thus, the DT formed by 916-912-917 may be selected in the process of centralizing. In contrast, the DT formed by 915-912-916 may not be selected.

Figure 10A:
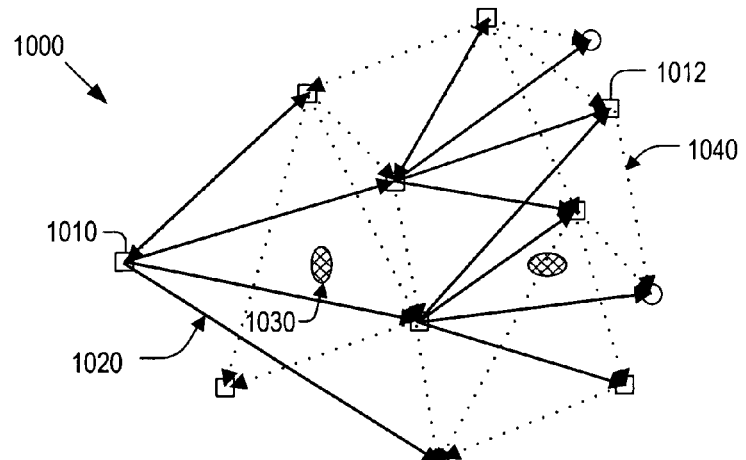
FIG. 10A illustrates progressively determining the locations of distributed anomalies by use of two directional ESRT trees formed in a directed graph as shown in FIG. 2B.

An embodiment may perform progressive interrogations for different progressive directions determined by multiple ESRTs. FIG. 10A illustrates progressive interrogation by use of two directional ERSTs 1020, 1040 built in the DT graph 1000 of an interrogation network so as to generate two dataset arrays of the location points of distributed anomalies 1030. Rotating the direction of each ESRT of an interrogation network may allow a collection of directional data arrays of the anomaly location points as well as the weights of SCI values corresponding to these location points.

Figure 10B:
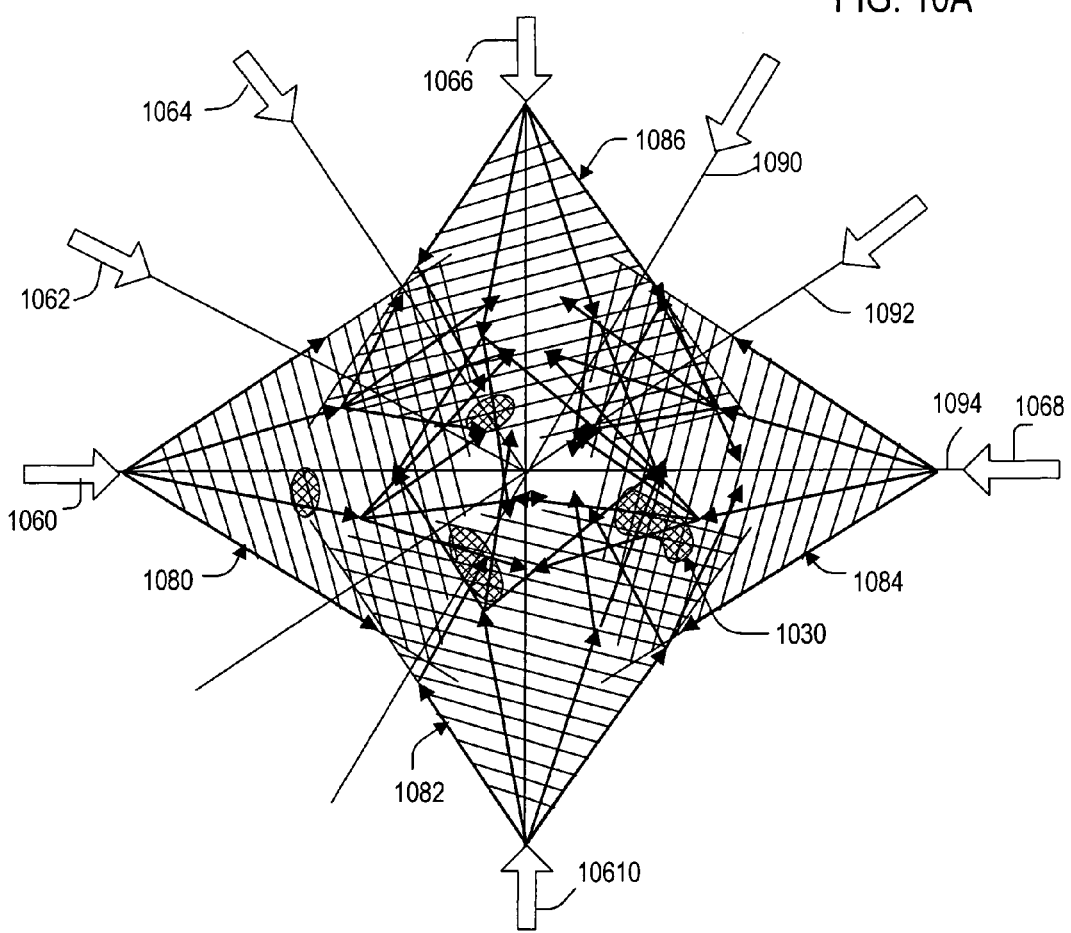
FIG. 10B illustrates obtaining tomography images of distributed anomalies by use of multiple directional ESRT trees formed in a directed graph as shown in FIG. 2B.

FIG. 10B illustrates obtaining tomography images of distributed anomalies by use of multiple directional ESRTs. By utilizing a parallel projection algorithm, an embodiment may generate a computed tomography for the directional data arrays corresponding to the ESRTs 1080-1086. To generate the computed tomography (CT) by the parallel projection algorithm, an interrogation 2-dim (or 3-dim) matrix for each of the ESRTs 1080, 1082, 1084, 1086 may be created by putting its column data or (2-dim data matrix of the projected locations) with the SCI weights at the location points of distributed anomalies 1030 that are determined at each directional angle. The directional ESRTs 1080, 1082, 1084, 1086 may be used to obtain the tomography image of distributed anomaly shapes by applying a parallel projection to the dataset determined at four mean directions 1060, 1066, 1068, 10610. To enhance the accuracy in determining the location and shape of the anomalies, additional ESRTs in the mean directions 1062, 1064, 1090, 1092 may be used. When projecting each directional ESRT to a project line (or plane), an embodiment may place the points of anomaly or object location along the project line (or surface) 1090, 1092, 1094, wherein each of project lines (or surface) 1090, 1092, 1094 may have as an origin the intersection point (or line) of the other project lines (or planes). An embodiment may generate interrogation matrices containing the information of distributed anomaly shapes for different directional views. Furthermore, an embodiment may generate a tomography image of the host structure with the receivers and transmitters arbitrarily distributed, which provides flexibility in arranging the patches on the host structure.

It is noted that the diagnostic patches of FIG. 10B may be randomly distributed on the host structure. In contrast, existing CT imaging techniques have a stringent constraint to collimate two transmitter and receiver arrays. Thus, the tree-based tomography imaging technique of FIG. 10B may be considered as a new CT imaging technique with enhanced flexibility in arranging the patches or patch sensors. The tree-based tomography imaging technique may also include the application of the parallel projection algorithm to any linked lists of planar graphs that can be configured by multi directional spanning trees in interrogation networks containing transmitters and receivers, or transceivers.

Figure 11:
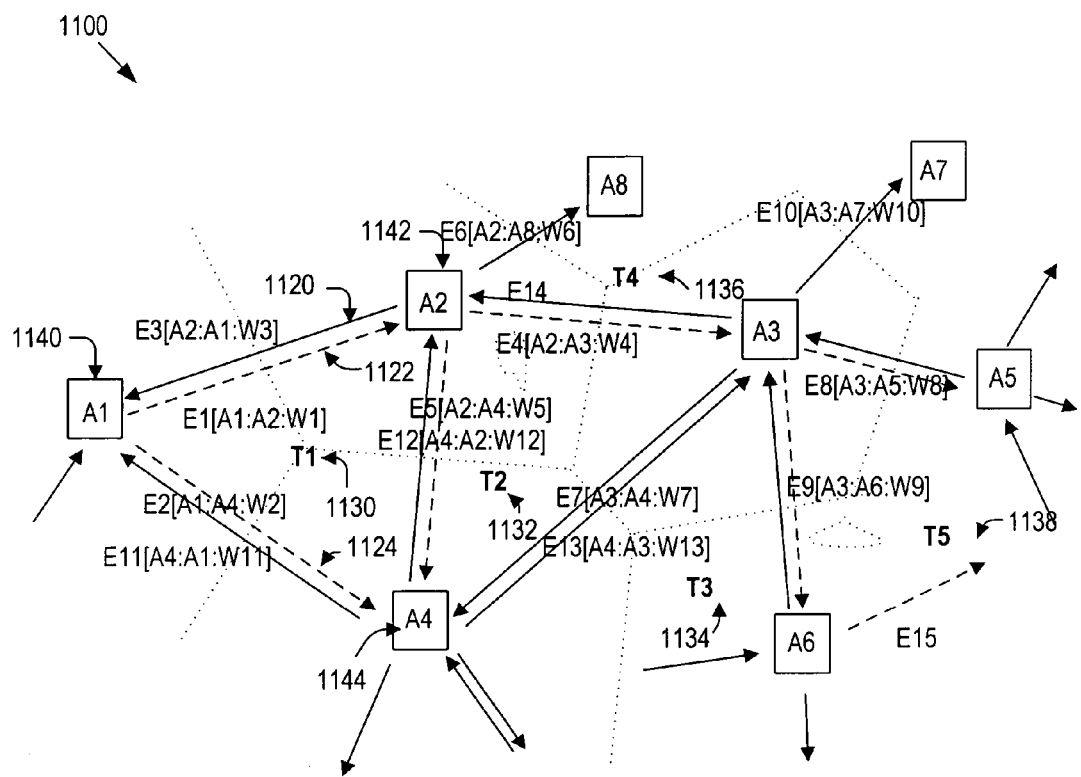
FIG. 11 shows a graph model for data association between multiple patches of FIG. 2B.
Figure 12:
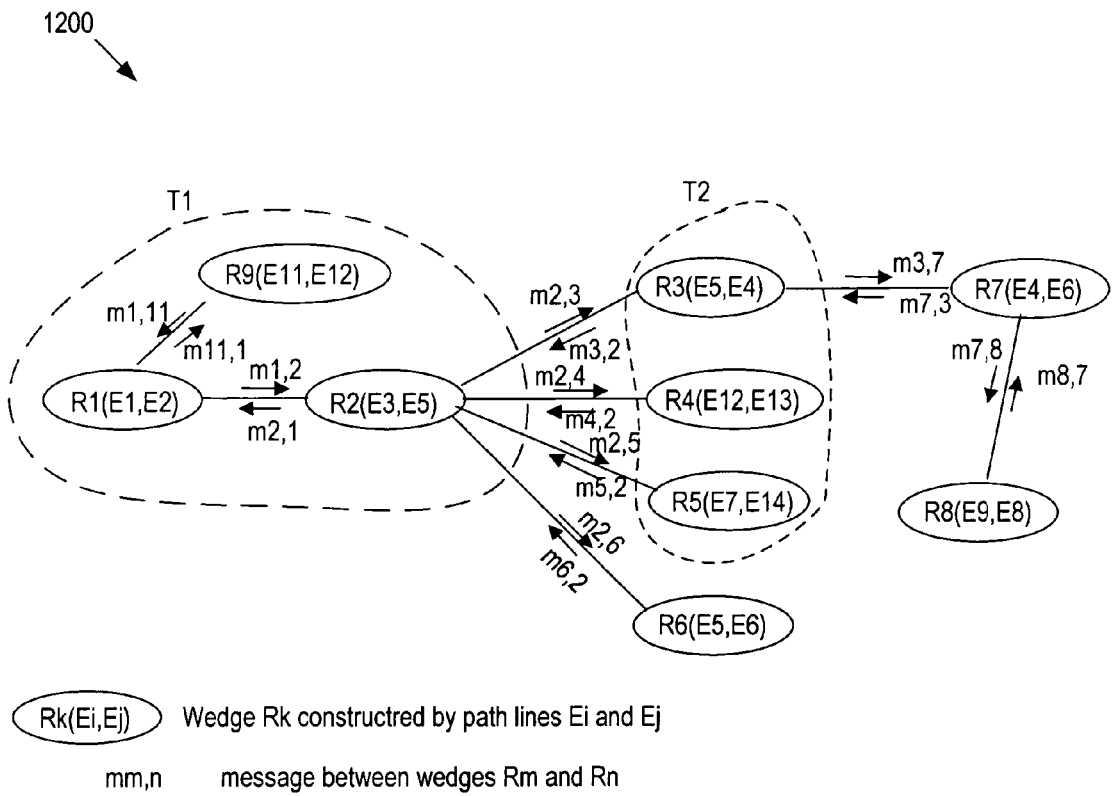
FIG. 12 shows a binary junction tree (BJT) graph corresponding to the graph model of FIG. 11.

An embodiment may execute data estimation and association to increase not only the correctness of SCI values against random noise signals, but also network adaptability to efficiently evolve in self-reconfiguring its network topology according to a pattern classification or system learning of interrogation networks. FIG. 11 shows a graph model 1100 for data association between multiple paths to enhance accuracy in analyzing sensor signals. As depicted, each edge is associated with one or more arrows indicating the direction of data association. For instance, the arrow 1120 may indicate that data association is directed between the edge E3 connecting a patch A2 1142 to a patch A1 1140, and the edge E11 connecting a patch A4 1144 to the patch A1 1140. The values of the weight associated with the edge E3 and E11 are W3 and W11. The data association may include the estimation of statistical dependence between SCI values or between weights of transmission paths. For DT wedges defined by two sides of DTs emanating from one actuator 1140 to two sensors 1142, 1144, an embodiment may construct a binary junction tree (BJT) graph consisting of a set of DT wedge nodes, or pairs of two DT sides 1122, 1124, and a set of the edges of each DT wedge pair comprising an DT. FIG. 12 shows a binary junction tree graph 1200 corresponding to the graph model 1100 of FIG. 11. As depicted, the node R1 is constructed by the edges E1 and E2 in FIG. 11. Each node of the BJT 1200 may exchange messages with at least one adjacent node if the node has a common edge with the adjacent one. Some of the nodes may be grouped into subgroups T1 and T2. An embodiment may allow the BJT graph 1200 to have the weights of the posteriori probability parameters in the adjacent matrix or adjacent linked lists corresponding to the graph. The parameters used in the BJT graph 1200 may be formulated by either a Bayesian network model or a Markov random field model. An embodiment may store each BJT edge of DT triangles in a data structure corresponding to DTs 1130-1138 as a reference to the estimation value of anomaly-location points and the identification numbers of neighboring DT triangles associated with the DT. The BJT graph may use a reference list of the data structures that store not only the sensor/actuator identification numbers but the flight-time delay and SCI values corresponding to each node.

An embodiment may perform data estimation to calculate accurate estimates of true SCI values bases on measured SCI values. An embodiment may utilize a minimum-mean-square-error (MMSE) estimation algorithm for the noisy measured SCI values of transmission paths by applying the estimation algorithm in local Delaunay triangulated graphs 1130-1138, instead of determining global and centralized estimations. The local correlations between SCI values may be encoded in a Delaunay triangulated graph since inter-path SCI correlations caused by anomaly may decay monotonically with distance away from the point of the anomaly position. The implementation of the SCI data estimation may include local minimum-mean-square-error (MMSE) estimation on each triangle and an exchange of the SCI estimates between neighboring paths and triangles. An embodiment may compute global data estimation by assembling each triangle matrix into the diagonal submatrix of a global estimation matrix for a planar DT graph.

An embodiment may transform data association to SCI inference problems so as to utilize a local message passing algorithm in interrogation networks. The BJT graph 1200 may include each wedge of DT as a node and a set of edges connecting the wedge of each triangle to the wedges of neighboring DTs. The message passing algorithm may be one of local message-passing algorithms on loopy graphs to provide the solutions of optimization problems such as maximum posteriori estimation. Also the algorithms may involve parallel message-passing operations in realizing the parallel processors of distributed network clusters, as illustrated in FIG. 13. In the algorithms, distributed inference may be calculated iteratively through the parallel exchange of information between neighboring nodes in the graph.

The massage-passing graph model 1200 may be an undirected graph containing a set V of nodes and a set E of edges, where each node s associates with a collection of random variables $x_s$ in Markov random field (MRF). An embodiment may use the MRFs with pair-wise compatibility functions defined only on individual nodes, or singleton cliques, and pairs of nodes joined by the edges. The p(x) of MRF distribution can be factorized as $$p(x) = \frac{1}{k} \prod_{s \in V} \psi_s(x_s) \prod_{(s,t) \in E} \psi_{st}(x_s, x_t),$$

where $\psi_s(x_s)$ is the node compatibility function that depend on only the individual variable $x_s$, $\psi_{st}(x_s, x_t)$ is the edge compatibility function that depend only on the variable $x_s$ and $x_t$ joined by edge (s, t), and k is a normalization constant. The random vector x of SCI values may not be observed. For given independent noisy observations y of SCI values, an embodiment may draw inference about x by transforming the prior p(x) to the conditional distribution p(x|y). An embodiment may estimate the marginal distribution $p(x_s)=\Sigma_{\{x'|x'_s=x_s\}} p(x')$ for each variable $x_s$, and find the maximum a posteriori (MAP) configuration $\hat{x}=\arg\max_x p(x)$. To compute the node marginal distribution $p(x_s)$, an embodiment may utilize either brief propagation algorithms or sum-product algorithms. The distribution may be given by the converged value of the message at node s via $$p(x_s) = k\psi_s(x_s) \prod_{t \in N(t)\backslash s} M^c_{st}(x_s)$$

where $M_{st}^c$ is the convergent value of each node after finite number of iteration on any tree-structured graph that is obtained by updating the message $M_{st}^n$, and N(t)\s is the set of neighbors of node t excluding node s. Also the message $M_{st}^n$ at nth iteration step may be given by $$M^n_{st}(x_s) = k \sum_{x_t} \left( \psi_{st}(x_s, x_t) \psi_t(x_t) \prod_{u \in N(t)\backslash s} M^{n-1}_{ut}(x_t) \right).$$

Also an embodiment may use another form of max-product algorithm to find the maximum marginals $P(x_s)=k \max_{\{x'|x'_s=x_s\}} p(x')$ at each node and the elements of MAP given by $\hat{x}_{s=arg\ max x_s} P_s(x'_s)$. The message in the max-product algorithm may be updated according to recursion $$M^n_{st}(x_s) = k \max_{x_t} \left( \psi_{st}(x_s, x_t) \psi_t(x_t) \prod_{u \in N(t)\backslash s} M^{n-1}_{ut}(x_t) \right).$$

The data association of SCI values in each path may be coupled with the other paths, due to the overlapping of interrogation regions covered by paths, and with the unknown nature of anomaly. It means that, to find the global data association, an embodiment may have to consider data association of all the jointed paths. However, instead attacking the data association problem of entire paths, an embodiment may concatenate a collection of local random association variables, wherein each variable is defined for each path corresponding to DTs.

An embodiment may allow the diagnostic network to adapt itself to the constraints, such as a delay or failure in detecting anomaly, as well as to the costs of signal computation and interrogation, such as limited processors and powers. To cope with these issues, an embodiment may run three phase steps. The first step corresponds to an initial phase in which transmission paths are generated by a random graph generator on a Voroni-diagram based network. The first step also includes setting up the interrogation network of Delaunay triangulation, obtaining interrogate signals for each path to estimate the average SCI values for entire paths, and adjusting the network paths to be a maximum anomaly-detection network by removing lower anomaly-detection routes from the network, and adding more paths to higher anomaly-detection routes. When an embodiment computes the initial average SCI values of each path, it can employ a message passing algorithm or local MMSE estimation algorithm.

In the second phase, most patches are in sleep or inactive state. The patches, called as "sentinels," may be awake and periodically transmit interrogation signals along higher anomaly-detection routes. Each sentinel patch may periodically interrogate the anomaly and provide its current SCI values of transmission paths. An embodiment may use these SCI values to perform a statistical hypothesis test to declare the presence of anomaly or continue interrogating. When a sentinel patch detects the presence of anomaly, it wakes up other patches in its vicinity to transmit interrogation signals by issuing an alert signal to them. In the third phase, after an anomaly has been detected, the patches that have been woken up may cooperate in message-passing data association and local MMSE estimation followed by the computation of location and shape of the anomaly.

Figure 13A:
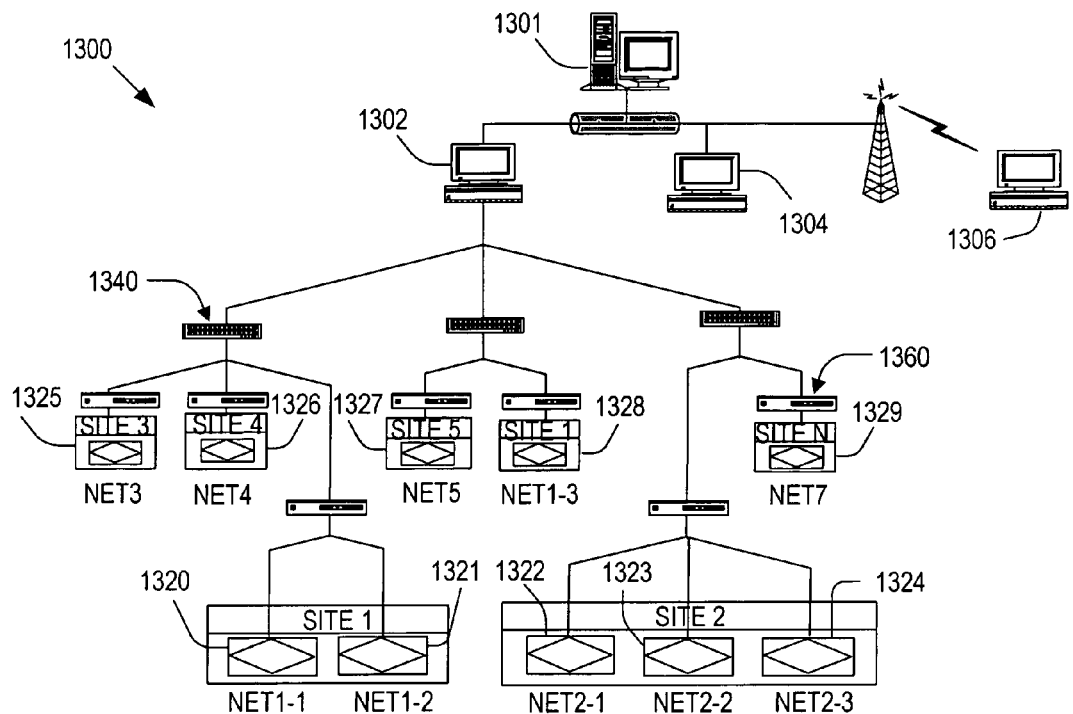
FIG. 13A shows a hierarchical architecture of distributed network clusters in accordance with another embodiment.

An embodiment may implement an interrogation monitoring schedule for operating diagnostic network clusters that are installed at separate portions of a host structure. FIG. 13A shows a hierarchical architecture 1300 of distributed interrogation network clusters in accordance with another embodiment. Hereinafter, the term interrogation system of the present disclosure collectively refers to the patches and software for operating the patches as described in conjunction with FIGS. 1A-17. Each of interrogation systems 1302, 1304, 1306 may include a switch module selector 1340 coupled to single networks 1325, 1326, 1327, 1328, 1329 via bridge boxes 1360. Each of the networks may include one or more subnetworks 1320, 1321, 1322, 1323, 1324. Also the interrogation system 1302, 1304, 1306 may be linked to an interrogation management system 1301 by Ethernet or wireless connection. Hereinafter, the term local network (or network clusters) collectively refers to networks 1325, 1326, 1327, 1328, 1329 and subnetworks 1320, 1321, 1322, 1323, 1324. Each network cluster 1320-1329 may be a local interrogation network to cover a portion of a structure or a site of structures, and may send a rate or warning level of structural condition of the sites. The interrogation system may receive structural condition rate (SCR) signal or warning level from each network cluster whenever each network cluster sends their SCR signal at the end of a time period of interrogation. The SCR signal may include information that can be the maximum deviation of either the SCI value of one specific transmission path or the averaged SCI value of a plurality of transmission paths, in a network cluster. The warning level on each network cluster may be determined by verifying its SCR according to the hypothesis test because the current SCR may vary at the end of every time slot of interrogation.

Figure 13B:
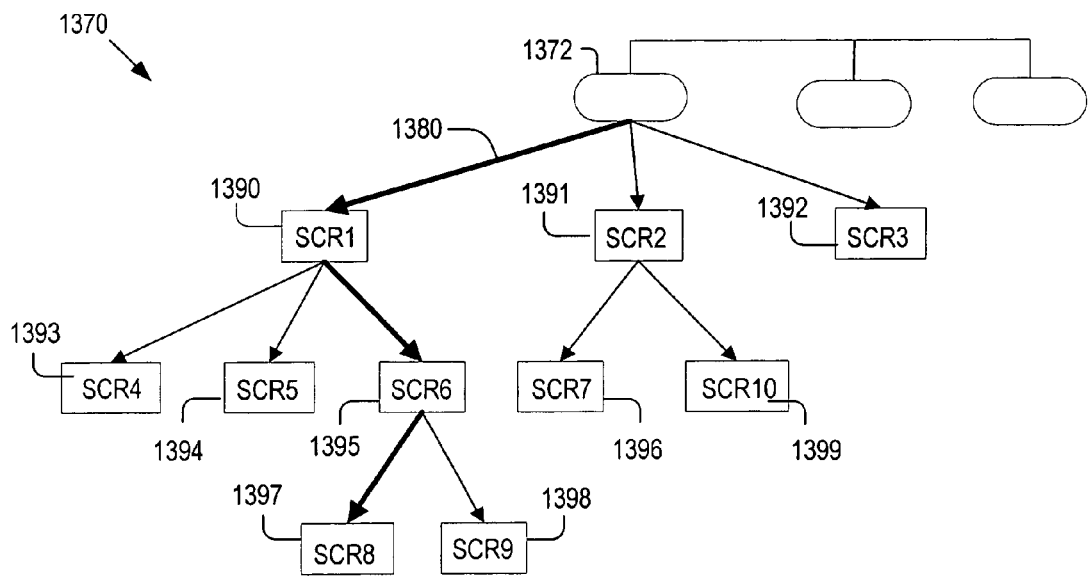
FIG. 13B shows a graph corresponding to the hierarchical architecture of FIG. 13A.

FIG. 13B shows a warning-level-tree graph 1370 corresponding to the hierarchical architecture 1300 of FIG. 13A. As depicted, the nodes 1390, 1391, 1392 may correspond to the switch module selectors 1340. Likewise, the nodes 1397 and 138 may correspond to the subnetworks 1320 and 1321. Each node may have a SCR value that corresponds to the maximum of the SCR values obtained from its child nodes. To ensure that all the warnings from the network clusters 1320-1329 are acknowledged, the interrogation system 1372 may allocate an interrogation time slot or period to each network cluster such that only one network cluster is active during each time slot. Then the quality of the interrogation schedule may be given by the number of clusters i such that for all $1 \leq j \leq i$, the set of interrogation clusters assigned time-slot j can detect all warnings. Furthermore, since the interrogation clusters 1372 may be left unattended after deployment, the interrogation system 1372 may utilize localized algorithms that can be easily adapted to provide a randomized algorithm that computes in one communication round a schedule. In the localized algorithms, each cluster 1390-1399 may decide by itself its time slot on the basis of its warning level, after exchanging information with its neighboring clusters.

For the scheduling of warning detection, the interrogation system corresponding to the architecture 1300 may utilize an algorithm adapted from domatic number by reiterating its random assignment on the time slots or a priority-first-search (PFS) algorithm applied in a warning-level tree graph 1370 of the data structure of SCR values that are recurrently generated in the network clusters 1390-1399, as illustrated in FIG. 13 B, so to allow longer interrogation-time slots to the network clusters 1380 that have higher warning levels.

As a variation, an embodiment may utilize a mincost-flow algorithm, an augmenting-route maxflow algorithm, or a network simplex algorithm to solve the assignment problems as well as the single-source-shortest-route problems in the adaptive interrogation-network configuration and evolution needed to be a self-learning interrogation systems In principle the embodiments of the present invention dedicates an interrogation system operably coupling ultrasonic or Lamb-wave transmitters and receivers that are not just attached to a structure, but also embedded in layered laminates and flexible layers, especially of distributed haptic or tactile sensors. Furthermore, the invention simply contemplates not only micro electric mechanical transmitters and receivers possibly used in a diagnosis system for human body as well as an artificial "nervous" system for robots, but also transmitting and receiving devices for any kinds of the interrogation signal transmission such as electrical magnetic, X-ray, light or laser, and infrared transmission instead ultrasonic transmission, in any manner that allow for analysis according to the methods described here.

Figure 14A:
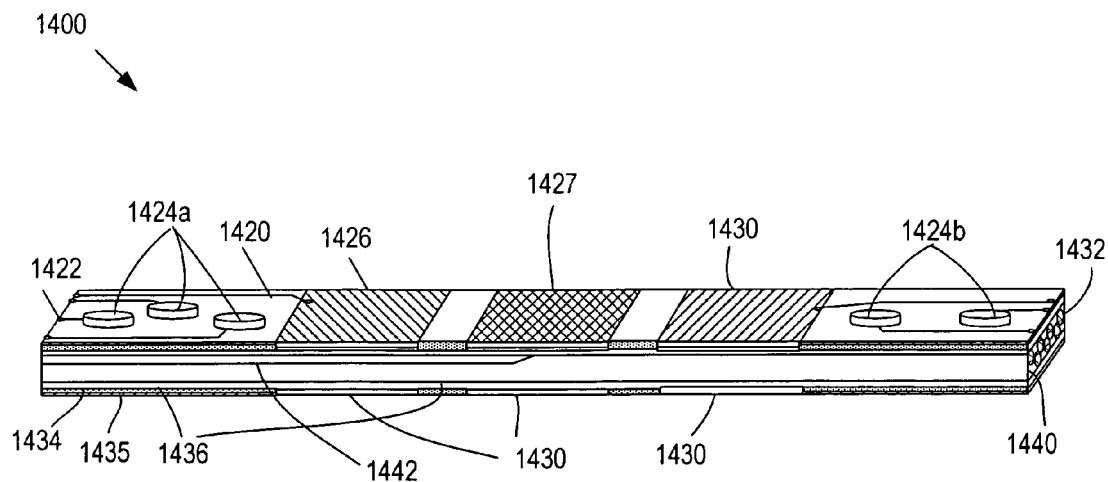
FIG. 14A shows an interrogation strip for detecting environmental conditions in accordance with another embodiment.

FIG. 14A shows an interrogation strip 1400 for detecting environmental conditions in accordance with another embodiment. As depicted, the interrogation strip may include a plastic string 1440 reinforced with carbon/glass-fibers 1432, a base metal layer 1436 coated over the plastic string 1440, a dielectric substrate layer 1434 coated over the base metal layer 1436, diagnostic network piezoelectric patches 1424 attached to the substrate layer 1434, a dielectric cover layer 1435 embedding electric metal clad wires 1420, the partial area of each electrical terminal 1422, and sensing segments 1426, 1427, 1430. The sensing segments can be a multicoated sensing device with coating layers containing plasma polymerized allylamine film, a platinum film in the sensing segment 1426 for detecting chemical reactions, coating layers containing sodium polysulfonesulfonate in the sensing segment 1427 for detecting humidity, coating layers containing gadolinium in the sensing segment 1428 for detecting Neutrons, and coating layers containing $TiO_2$ film in the sensing segment 1430 for detecting biological reactions. The sensing segments may measure environmental gas, neutron, and bio agent between the diagnostic patches 1424a and 1424b. Without limiting the scope of the present invention, the interrogation strip 1400 can be a type of circular wire or rod containing any kind of multiple coating layers for monitoring environmental conditions.

Figure 14B:
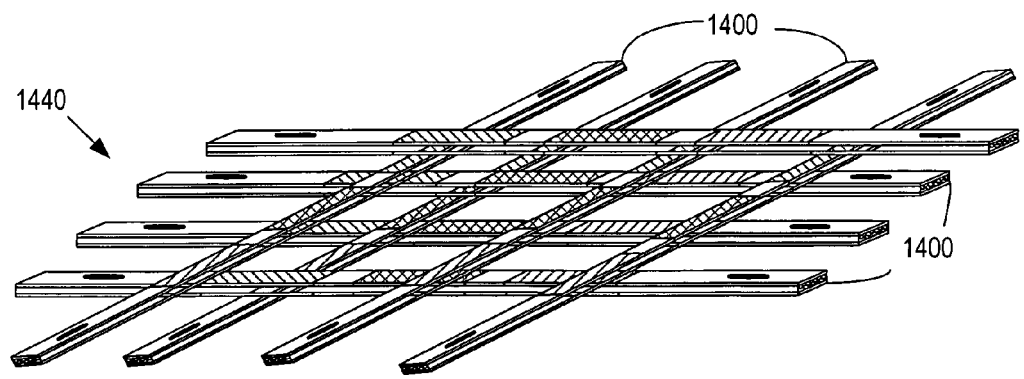
FIG. 14B shows a net of interrogation strips in FIG. 14A.

An embodiment may implement an environment interrogation network by building a net 1440 of interrogation strips 1400 as shown in FIG. 14B. The net 1440 may contain the acoustic transceivers 1424a, b at their end nodes or junction points of strips. The network 1440 may be a surface acoustic wave (SAW)-based sensory network.

Figure 15:
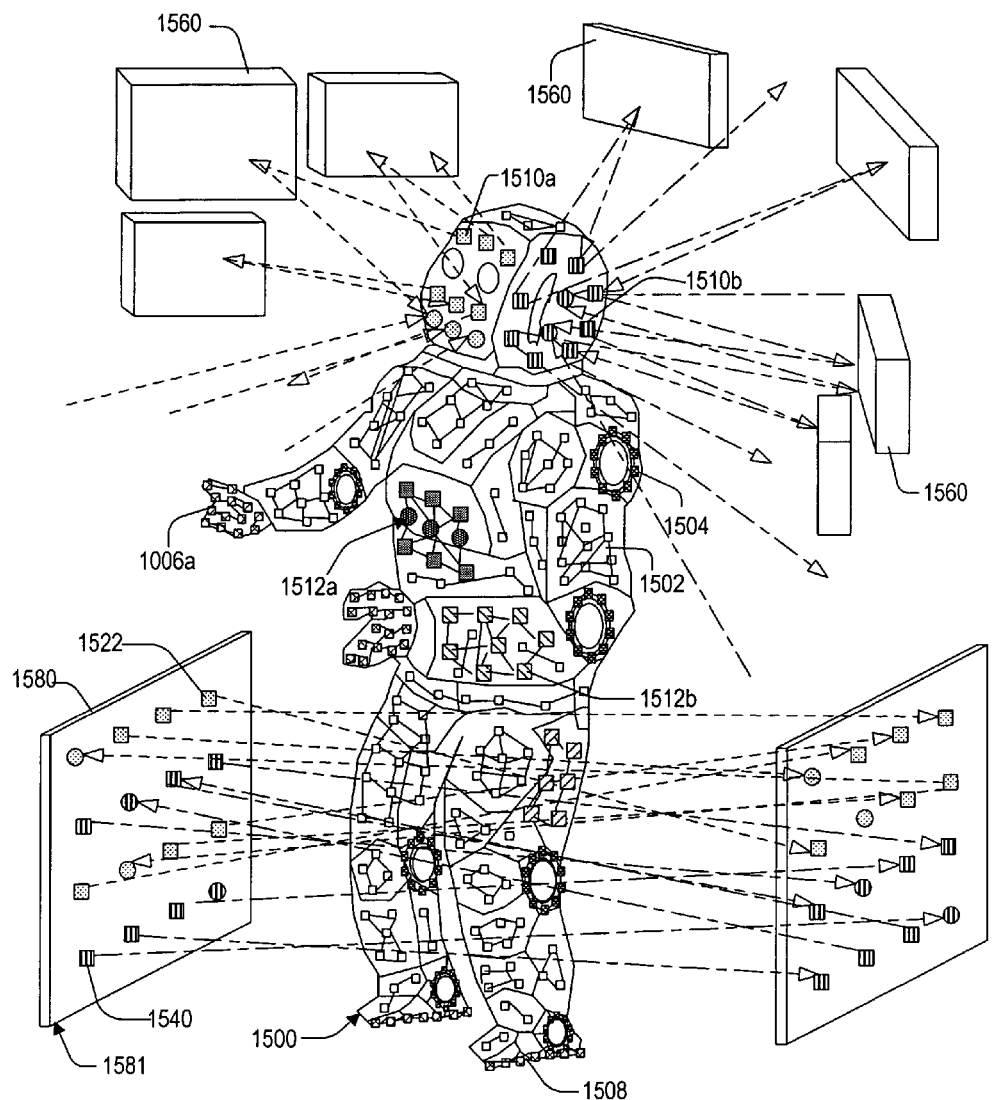
FIG. 15 shows a humanoid robot having interrogation networks for detecting damages, articulation loads, tactile pressure, foot-loads, and obstacles, and an intrusion/inspection interrogation network in accordance with another embodiment.

FIG. 15 shows a humanoid robot 1500 having interrogation networks for detecting damages, articulation loads, tactile pressure, foot-loads, and obstacles 1560, and an intrusion/inspection interrogation network 1580 in accordance with another embodiment. Planar interrogation networks 1502 embedded in structural parts of the robot 1500 can be used to detect anomaly and damage of the parts by transmitting and receiving acoustic or Lamb-wave signals with acoustic transceivers. Also, articulation interrogation networks 1504 forming a plurality of circular-shape networks and being embedded or attached along the circumferential guide of housing ring or a case of articulation joints, such as pin or hinge, sliding or gliding, pivot, and ball-and-socket joints, can be used to measure multidirectional mechanical load distribution at each articulation point of the robot and thereby to allow accurate dynamic control of the robot 1500. Without limiting the scope of the present invention, the articulation interrogation network 1504 exploiting acoustic signal transmissions can be used in any bearings to measure the load distribution and to monitor the fault of its components. Furthermore, a haptic or tactile interrogation network 1506 exploiting preferably acoustic transmissions can be used to measure pressure, temperature at contact locations and thereby to allow the robot 1500 to respond to external stimuli. The haptic or tactile interrogation network 1506 may implement a weaving net 1440 and, as a variation, may use a mesh net of conductive-ink lines painted on the structure to exploit electric signal transmissions instead of acoustic signal transmissions. The environment interrogation networks 1512a, 1512b can be implanted in the robot 1500 by attaching one or more weaving nets 1440 for monitoring toxic gas or neutrons.

Hirosh et al. discloses ankle joints of biped robots in U.S. Pat. No. 6,377,014, which is incorporated by reference in its entirely. The Hirosh et al. robot contains two articulated legs and feet. Each foot of the robot has front and rear rubber bushes as elastic adaptors to absorb impacts on the ankle. Leonide Marslov and Son Young disclose in Korean Patent Applications 10-2004-0007855 and 10-2004-0022036a walking robot having two articulated legs, wherein these applications are incorporated by reference in their entirely. The Marslov et al. robot has two feet, each foot consisting four segmented base plates with rubber bushes and force sensors in the front two base plates of the foot so as to provide a shock-absorbing and stabilization mechanism. A foot interrogation network 1508 that measure load distribution of multi-segmented shock-absorber pieces for toe joints of the foot can be used to acquire landing surface positions and to provide dynamic stability during biped walking. Specially, for the interrogation network including a weaving net of metal and carbon/glass-fiber reinforced plastic strips or wires, can be embedded in each rubber bush or affixed between rubber bushes and metal plate pieces of the foot. The weaving net can build an interrogation network to detect the change of interrogation signals due to foot contact pressure to the floor. The weaving net used for the foot interrogation network may contain acoustic transceivers at their terminal points of strips.

Spatial response interrogation networks 1510a and 1510b may include the nodes of transceivers affixed to the robot, and the transmission paths of interrogation signals emitted from the transceivers to the outside of the structure. The interrogation signal can be a laser beam 1510a or an acoustic and infrared beam of 1510b projected from signal transmitters and received by signal receivers. An obstacle 1560 reflecting incident interrogation signals can be considered as another virtual transceiver of the interrogation signals as explained in FIG. 3 and FIG. 4. Each bi-directional path from one transmitter to the obstacle and from the obstacle to one of receivers may be used in the network. The interrogation paths with non-reflected or non-response transmission with the respect to the querying signals emitted from actuators can be considered as a single directed path from unknown transmitter or receivers such that these unknown nodes are defined as latent nodes located away from the network dimension with infinity path distance. The spatial response interrogation network, comprising the nodes of multiple transmitters and receivers attached to the robot and their transmission paths coupled to neighboring spatial obstacles, can be used as a navigation system of the robot and a mechanism to track trajectories of mobile objects.

An embodiment may implement an intrusion detection network 1581 having a plurality of the transmitters and receivers attached to a structure wall 1580 and using laser or acoustic beams to detect an object when the object blocks one or more interrogation signal transmissions. The intrusion detection network 1522 can adapt recursively pairing transmitters and receivers to get the high occurrence of blocking interrogation signal transmission. While the intrusion detection network is adapting, the projection angle and receiving angle of the transducers can be changed to provide high probability of intrusion detection. The embodiment may also implement an inspection interrogation network 1540 utilizing a plurality of the X-ray transmitters and receivers attached the structure wall 1580 to monitor interior components of the object in a container for inspection and security.

Figure 16:
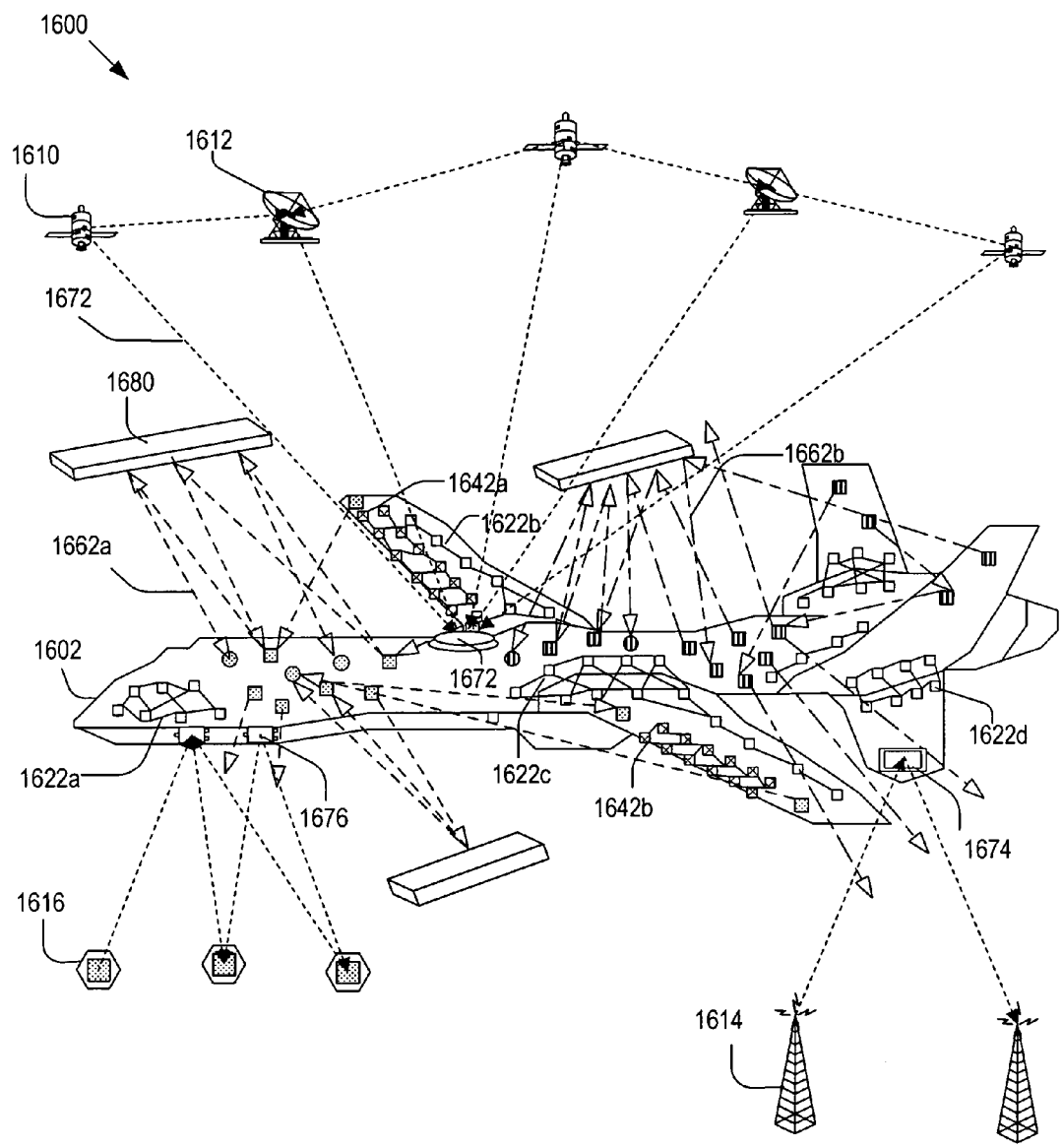
FIG. 16 shows a mobile system having interrogation networks for monitoring structural conditions of the mobile system and detecting objects around the mobile system in accordance with another embodiment.

FIG. 16 shows a mobile interrogation system 1600 containing various interrogation networks implemented in a mobile system 1602, as another example of the application of interrogation networks. A planar interrogation networks 1622a-d embedded in structural parts of the mobile system can be used to detect anomaly and damage of the parts by transmitting and receiving acoustic or Lamb-wave signals with acoustic transceivers. A regional-sensing interrogation network 1642a-b exploiting preferably acoustic transmissions can be used to measure pressure and temperature of the system 1602. Furthermore, spatial response interrogation networks 1662a-b may be implemented by including the nodes of transceivers affixed to the mobile system 1602, and the transmission paths of interrogation signals emitted from the transceivers attached to the surface of the mobile system to the outside of the system. The interrogation signal can be laser beams 1662a, electric magnetic beams 1662b projected from the signal transmitters and received by the signal receivers. Mobile obstacles 1680 reflecting incident interrogation signal can be considered as another virtual transceiver of the interrogation signals as explained in FIG. 3 and FIG. 4. Each bi-directional path may include a path from one transmitter to the obstacle and another path from the obstacle to one of receivers. An embodiment may implement a positioning interrogation network 1672 containing Global Positioning Satellite (GPS) receivers 1672, radio frequency Identification (RFID) transponders or tags 1676, and reckon transceivers 1674 attached to the mobile system that communicate position data transmitted from GPS satellites 1610, antennae 1612, RFID transceivers 1616, or reckon systems 1614.

Figure 17:
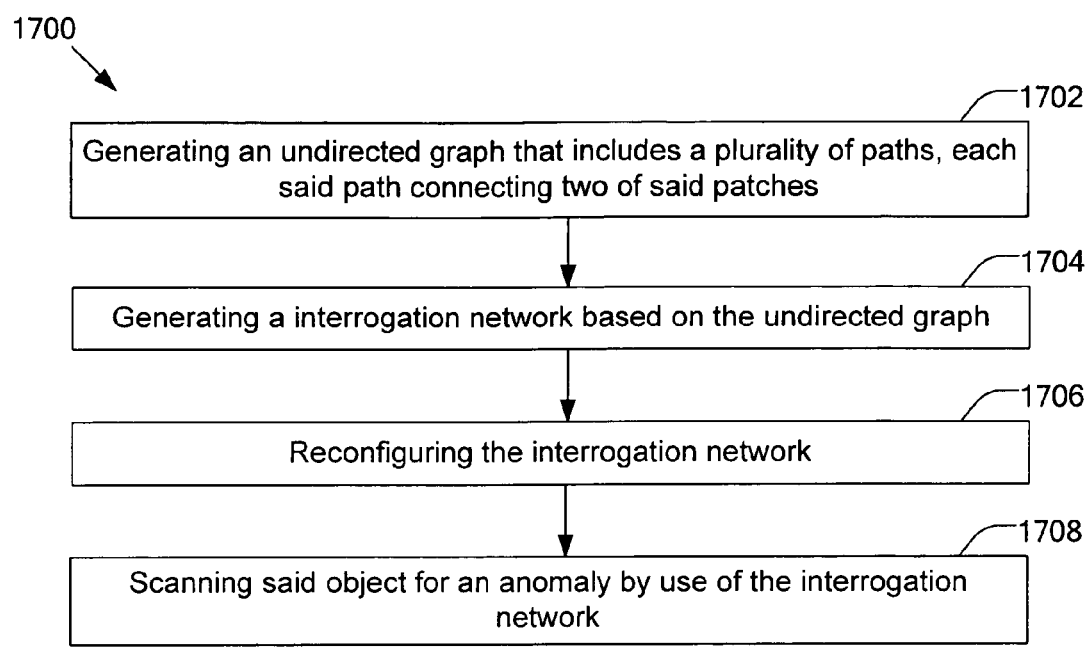
FIG. 17 is a flow chart illustrating exemplary steps for operating an interrogation system in accordance with another embodiment.

FIG. 17 is a flow chart 1700 illustrating exemplary steps for operating an interrogation system in accordance with another embodiment. The interrogation system may include a plurality of patch sensor attached to a host structure. In a state 1702, an undirected graph that includes a plurality of paths for connecting the patch sensors may be generated. Then, a directed graph or network may be generated based on the undirected graph in a state 1704. Next, in a state 1706, the network may be reconfigured. Subsequently, the host structure may be scanned for anomalies in a state 1708.

When an interrogation system builds appropriate graphs to abstract the data structures of patches and transmission paths for the application of algorithms explained in the embodiments of the present teachings, it is necessary to implement transparent persistency between abstracted data objects and a relational (SQL) database management system. An embodiment may implement an object model working as database access layer that is the content of abstracted data objects contained classes. An embodiment may create a mapping between object oriented model and relational DB model, and it may automate the computation of this mapping by describing a natural encoding for this mapping. For the transparent persistency, it may also create an abstraction layer that separates the objects from the methods responsible for ensuring the persistence of the objects. For example, the "DNP entity" interface may be used to define the structure of data objects corresponding to interrogation graphs. The interface of DNP tuple may be associated with rows in a relational database management system (RDBMS) table for a DNP entity by creating a new data tuple that is not yet contained in the RDBMS and retrieving a specific set of tuples from a table of RDBMS. An embodiment may also create query evaluator class for the retrieval and modification of all relevant data specified by a query, and query factory class for dynamically generating SQL statements according to a set of given parameters and constructors.

Certain embodiments may be implemented in extensible Markup Language (XML) web services, which are capable of communicating and remote computing, by using the open standard Simple Object Access Protocol (SOAP) or XML-Remote-procedure Calls (RPC) with XML-formatted documents. The methods of interrogation transmission networking may be abstracted as an entity by use of Common Object Module (COM), and SOAP wrapper to provide Internet web services. An embodiment may allow the data structures and objects of interrogation networks to be accessed in a mobile system that utilize wireless application protocol (WAP) interface with wireless markup language (WML). An embodiment may include a web access of any mobile or web-enabled devices to the data processed by certain embodiments and stored in the database of an interrogation network system.

While the present invention has been described with reference to the specific embodiments thereof, it should be understood that the foregoing relates to preferred embodiments of the invention and that modifications may be made without departing from the spirit and scope of the invention as set forth in the following claims.

What is claimed is:

1. A method of operating an interrogation system that includes a plurality of patches secured to an object, each said patch being adapted to operate as at least one of a transmitter patch for generating a diagnostic wave that propagates in the object and a sensor patch for developing a sensor signal in response to said diagnostic wave, said method comprising:
    arranging the plurality of patches in an undirected graph including a plurality of paths, each said path being an edge of the undirected graph and connecting two of said patches that correspond to nodes of the undirected graph;
    measuring, by use of the patches, a quantity associated with a diagnostic wave propagating along each said path in the undirected graph, said quantity including at least one of a time-of-arrival, an amplitude, and an energy of the diagnostic wave;
    comparing the measured quantity with a baseline quantity to determine a deviation therebetween, the baseline quantity being measured by use of the patches in absence of structural anomaly; and
    analyzing the deviation to determine an anomaly.

2. A method as recited in claim 1, wherein said anomaly is selected from the group consisting of hole, crack, repair patch, local change in the temperature of said object, local change in the pressure applied to said object, and a body outside of said object.

3. A method as recited in claim 1, wherein said undirected graph is a Euclidean graph and the length of each said path is shorter than a preset value.

4. A method as recited in claim 3, wherein the step of generating an undirected graph includes:
    generating a Voroni diagram for optimizing the distribution of said patches; and
    generating a Delaunay diagram including Delaunay triangles.

5. A method as recited in claim 4, wherein at least one selected from the group consisting of a randomized incremental algorithm, a divide-and-conquer algorithm, and a plane sweep algorithm, is used to generate said Voroni diagram.

6. A method as recited in claim 4, wherein at least one selected from the group consisting of a two-dimensional binary tree search algorithm, a near neighbor search algorithm, and a two-dimensional grid range search algorithm, is used to search, insert, or delete one or more of the diagnostic patches of said Voroni diagram.

7. A method as recited in claim 4, wherein a locally equiangular triangulation technique is used to generate said Delaunay diagram.

8. A method as recited in claim 4, wherein said Delaunay diagram includes a Euclidean minimum spanning tree (EMST) and wherein one of Kruskal's algorithm and priority-first-search of Prim's algorithm is used to perform graph searching of said EMST.

9. A method as recited in claim 4, wherein said object includes at least one obstacle that has obstacle vertices and said paths include line segments of said Delaunay triangles connecting said patches and said obstacle vertices.

10. A method as recited in claim 4, wherein said object includes one or more obstacles, said paths include a visibility graph, and a Dijkstra algorithm is used to generate the visibility graph.

11. A method as recited in claim 4, wherein said object includes one or more obstacles that have obstacle vertices, said Delaunay diagram includes one or more passable channels formed between said obstacles, each said passable channel includes one or more of said patches, and only one of said patches is located within a circle that passes two of said obstacle vertices.

12. A method as recited in claim 4, wherein said object includes at least one obstacle and wherein at least one of said paths is generated by one of beam tracing and ray tracing techniques and represents a trajectory of a signal reflected on the boundary of said object.

13. A method as recited in claim 4, wherein said object includes at least one obstacle and wherein at least one of said paths is generated by the steps of:

dividing an area covered by said interrogation system into spatial subdivisions, each said spatial subdivision having a rectangular shape;

selecting a first one of said spatial subdivisions as an actuator subdivision and a second one of said spatial subdivisions as a sensor subdivision, said actuator subdivision including a patch capable of generating a diagnostic wave;

traversing said spatial subdivisions to determine a plurality of subdivision sequences, each said subdivision sequence including a set of contiguous spatial subdivisions and starting from said actuator subdivision to said sensor subdivision; and selecting one of said subdivision sequences that has the maximum structural condition index value change due to said at least one obstacle.

14. A method as recited in claim 4, wherein said object includes at least one obstacle and wherein at least one of said paths is generated by the steps of:

dividing a space covered by said interrogation system into spatial subdivisions, each said spatial subdivision having a cubical shape;

selecting a first one of said spatial subdivisions as an actuator subdivision and a second one of said spatial subdivisions as a sensor subdivision, said actuator subdivision including a patch capable of generating a diagnostic wave;

traversing said spatial subdivisions to determine a plurality of subdivision sequences, each said subdivision sequence including a set of contiguous spatial subdivisions and starting from said actuator subdivision to said sensor subdivision; and selecting one of said subdivision sequences that has the maximum structural condition index value change due to said at least one obstacle.

15. A method as recited in claim 4, wherein said object includes a plurality of obstacles and wherein at least one of said paths is generated by ray mirror method and represents a trajectory of a signal reflected on the boundaries of said obstacles.

16. A method as recited in claim 3, further comprising:
determining the diameter of said undirected graph.

17. A method as recited in claim 16, further comprising:
dividing said undirected graph if said diameter is larger than a preset limit.

18. A method as recited in claim 1, wherein said undirected graph is non-weighted, further comprising:
determining a shortest route for each pair of said patches in said undirected graph by use of a recursive depth-first-search (DFS) method.

19. A method as recited in claim 18, further comprising:
deleting said shortest route.

20. A method as recited in claim 1, wherein each of said paths is associated with a weight, said weight being one selected from the group consisting of the physical length of a path, a time-of-flight for a diagnostic wave to travel a path, and a change in a measured structural condition index (SCI) value of a path due to said anomaly.

21. A method as recited in claim 20, wherein said undirected graph is weighted, further comprising:
determining a shortest route for each pair of said patches in said undirected graph by use of a breadth-first-search (BFS) method.

22. A method as recited in claim 21, further comprising:
deleting said shortest route.

23. A method as recited in claim 20, wherein said undirected graph is weighted and said weight is the change in the measured SCI value, further comprising:
determining modified minimum spanning trees (MMSTs) for each said patch in said undirected graph, said MMSTs including a first tree that has a minimum total weight and a second tree that has a maximum total weight.

24. A method as recited in claim 23, wherein said MMSTs are generated by use of Boruvaka's algorithm.

25. A method as recited in claim 23, wherein said MMSTs are Euclidean MMSTs and the longest route in each MMST is an indicator of the area covered by said interrogation system and the sparsity of said undirected graph.

26. A method as recited in claim 23, further comprising:
deleting a portion of said first MMST from said undirected graph; and
adding at least one path to said undirected graph.

27. A method as recited in claim 20, further comprising:
adding one or more paths nearby selected ones of said paths, wherein the weights of said selected paths are larger than a preset value.

28. A method as recited in claim 1, further comprising:
generating a transitive closure of said undirected graph; and
checking reachability between said patches by use of said transitive closure.

29. The method of claim 1, wherein the sensor signal includes at least one of ultrasonic wave, Lamb wave, vibrational wave, acoustic wave, and electromagnetic wave and wherein the electromagnetic wave includes laser light and X-ray beams.

30. The method of claim 29, wherein the electromagnetic wave further includes radar wave and ultra-wideband(UWB) impulse.

31. A method of operating an interrogation system that includes a plurality of patches secured to an object, each said patch being adapted to operate as at least one of a transmitter patch for generating a diagnostic wave that propagates in the object and a sensor patch for developing a sensor signal in response to said diagnostic wave, said method comprising:

arranging the plurality of patches in a directed graph including a plurality of paths, each said path being an edge of the directed graph and connecting two of said patches that correspond to nodes of the directed graph, said directed graph forming a network of the diagnostic wave transmission;

measuring, by use of the patches, a quantity associated with a diagnostic wave propagating along each said path in the directed graph, said quantity including at least one of a time-of-arrival, an amplitude, and an energy of the diagnostic wave;

comparing the measured quantity with a baseline quantity to determine a deviation therebetween, the baseline quantity being measured by use of the patches in absence of structural anomaly; and analyzing the deviation to determine an anomaly.

32. A method as recited in claim 31, wherein each of said paths is associated with a weight, said weight being one selected from the group consisting of the physical length of a path, a time-of-flight for a diagnostic wave to travel a path, and a change in a measured structural condition index (SCI) value of a path due to said anomaly.

33. A method as recited in claim 32, wherein said directed graph is weighted, further comprising:
determining modified shortest route trees (MSRTs) for each said patch in said directed graph, said MSRTs including a first tree that has a minimum total weight and a second tree that has a maximum total weight.

34. A method as recited in claim 33, wherein at least one selected from the group consisting of Dijkstra's algorithm and Bellman-Ford's algorithm is used to generate said MSRTs.

35. A method as recited in claim 33, wherein Floyd's algorithm is used to search all maximum and minimum anomaly-detection routes in said directed graph and to generate all shortest interrogation routes.

36. A method as recited in claim 33, wherein said directed graph is weighted, further comprising:
for each pair of patches, determining a maximum anomaly-detection route end a minimum anomaly-detection route using one selected from the group consisting of a min-cost-flow algorithm, an augmenting-route maxflow algorithm, and a network simplex algorithm.

37. A method as recited in claim 36, further comprising:
deleting a portion of said minimum anomaly-detection route; and
adding at least one path to said directed graph.

38. The method of claim 31, wherein the sensor signal includes at least one of ultrasonic wave, Lamb wave, vibrational wave, acoustic wave, and electromagnetic wave and wherein the electromagnetic wave includes laser light and X-ray beams.

39. The method of claim 38, wherein the electromagnetic wave further includes radar wave and ultra-wideband (UWB) impulse.

40. A method as recited in claim 31, further comprising:
dividing said directed graph into strong components;
building a kernel of said directed graph based on said strong components;
computing a transitive closure of said kernel; and
checking whether or not the directed graph includes a cyclic route based on said transitive closure.

41. A method as recited in claim 31, further comprising:
scheduling a sequence of said paths by topologically sorting said directed graph.

42. A method as recited in claim 31, further comprising:
(a) discriminating said directed graph into several networks according to a set of weight levels;
(b) generating all-pairs shortest routes for each said network;
(c) repeating said steps (a) and (b) at a plurality of points in time; and
(d) detecting an evolution of said anomaly by comparing the all-pairs shortest routes of said discriminated networks with each other.

43. A method as recited in claim 42, wherein at least one selected from the group consisting of Bellman-Ford algorithm and Floyd's algorithm is used to determine said all-pairs shortest routes.

44. An interrogation system, comprising:
a plurality of patches adapted to be secured to an object, each said patch being adapted to operate as at least one of a transmitter patch for generating a diagnostic wave that propagates in the object and a sensor patch for developing a sensor signal in response to said diagnostic wave; and
a processor coupled to the patches and operative to generate an undirected graph that includes a plurality of paths, each said path being an edge of the undirected graph and connecting two of said patches that correspond to nodes of the undirected graph, to measure, by use of the patches, a quantity associated with a diagnostic wave propagating along each said path in the undirected graph, to compare the quantity with a baseline quantity measured by use of the patches in absence of structural anomaly to thereby determine a deviation therebetween, and to analyze the deviation to determine an anomaly,
wherein said quantity includes at least one of a time-of-arrival, an amplitude, and an energy of the diagnostic wave.

45. An interrogation system, comprising:
a plurality of patches adapted to be secured to an object, each said patch being adapted to operate as at least one of a transmitter patch for generating a diagnostic wave that propagates in the object and a sensor patch for developing a sensor signal in response to said diagnostic wave; and
a processor coupled to the patches and operative to generate a network that includes a plurality of paths, each said path being an edge of the network and connecting two of said patches that correspond to nodes of the network, to measure, by use of the patches, a quantity associated with a diagnostic wave propagating along each said path in the network, to compare the quantity with a baseline quantity measured by use of the patches in absence of structural anomaly to thereby determine a deviation therebetween, and to analyze the deviation to determine an anomaly,
wherein said quantity includes at least one of a time-of-arrival, an amplitude, and an energy of the diagnostic wave.

* * * * *